(12) United States Patent
Bukhman

(10) Patent No.: US 8,172,759 B2
(45) Date of Patent: May 8, 2012

(54) METHODS AND SYSTEMS FOR DETECTING EPILEPTIC EVENTS USING NONLINEAR ANALYSIS PARAMETERS

(75) Inventor: Vladislav Bukhman, East Northport, NY (US)

(73) Assignee: Cyberonics, Inc., Houston, TX (US)

( * ) Notice: Subject to any disclaimer, the term of this patent is extended or adjusted under 35 U.S.C. 154(b) by 293 days.

(21) Appl. No.: 12/429,746

(22) Filed: Apr. 24, 2009

(65) Prior Publication Data

US 2010/0274303 A1    Oct. 28, 2010

(51) Int. Cl.
*A61B 5/0205* (2006.01)
(52) U.S. Cl. .......................... 600/483; 607/45; 600/509
(58) Field of Classification Search .................. 600/483, 600/508, 509, 544; 607/2, 3, 45
See application file for complete search history.

(56) References Cited

U.S. PATENT DOCUMENTS

| | | | | |
|---|---|---|---|---|
| 4,867,164 A | 9/1989 | Zabara | | 128/421 |
| 4,979,511 A | 12/1990 | Terry, Jr. | | 128/642 |
| 5,025,807 A * | 6/1991 | Zabara | | 607/45 |
| 5,188,104 A | 2/1993 | Wernicke et al. | | 128/419 R |
| 5,215,086 A | 6/1993 | Terry, Jr. et al. | | 128/421 |
| 5,231,988 A | 8/1993 | Wernicke et al. | | 128/421 |
| 5,263,480 A | 11/1993 | Wernicke et al. | | 607/118 |
| 5,269,303 A | 12/1993 | Wernicke et al. | | 607/45 |
| 5,299,569 A | 4/1994 | Wernicke et al. | | 607/45 |
| 5,304,206 A | 4/1994 | Baker, Jr. et al. | | 607/2 |
| 5,330,515 A | 7/1994 | Rutecki et al. | | 607/46 |
| 5,335,657 A | 8/1994 | Terry, Jr. et al. | | 607/45 |
| 5,571,150 A | 11/1996 | Wernicke et al. | | 607/72 |
| 5,707,400 A | 1/1998 | Terry, Jr. et al. | | 607/44 |
| 5,916,239 A | 6/1999 | Geddes et al. | | 607/14 |
| 5,978,702 A * | 11/1999 | Ward et al. | | 607/3 |
| 6,337,997 B1 * | 1/2002 | Rise | | 607/45 |
| 6,587,719 B1 | 7/2003 | Barrett et al. | | 607/2 |
| 6,609,025 B2 | 8/2003 | Barrett et al. | | 607/2 |
| 6,622,041 B2 | 9/2003 | Terry, Jr. et al. | | 607/9 |
| 7,225,013 B2 * | 5/2007 | Geva et al. | | 600/513 |
| 7,276,026 B2 * | 10/2007 | Skinner | | 600/300 |
| 7,570,999 B2 | 8/2009 | Libbus et al. | | |
| 2005/0149157 A1 | 7/2005 | Hunter et al. | | |
| 2005/0234307 A1 * | 10/2005 | Heinonen et al. | | 600/300 |
| 2007/0219455 A1 * | 9/2007 | Wong et al. | | 600/515 |
| 2008/0234780 A1 | 9/2008 | Smith et al. | | |
| 2008/0319281 A1 * | 12/2008 | Aarts | | 600/301 |
| 2009/0124870 A1 * | 5/2009 | Arends et al. | | 600/301 |

OTHER PUBLICATIONS

Loncar-Turukalo et al.; "Measures of Deterministic Dynamics of Heart Rate and Blood Pressure Signals in Rats"*Acta Polytechnica Hungarica* 5(1):121-133; ISSN 1785-8860 (2008).
Zochowski et al., "Autocorrelations of R-R distributions as a measure of heart rate variability;" *Physical Review E* 56:3725-3727 (1997).

* cited by examiner

*Primary Examiner* — Carl H Layno
*Assistant Examiner* — Eugene Wu
(74) *Attorney, Agent, or Firm* — Cyberonics, Inc.

(57) ABSTRACT

Disclosed herein are methods, systems, and apparatus for detecting an epilepsy event in a patient using a medical device. The medical device is capable of determining an occurring epilepsy event, for example a seizure or an increased risk of a seizure. The determination is performed by determining at least one nonlinear analysis parameter associated with the beat sequence of the patient's heart. The medical device may then take a responsive action, such as warning, logging the time of the seizure, computing and storing one or more seizure severity indices, and treating the epilepsy event.

32 Claims, 16 Drawing Sheets

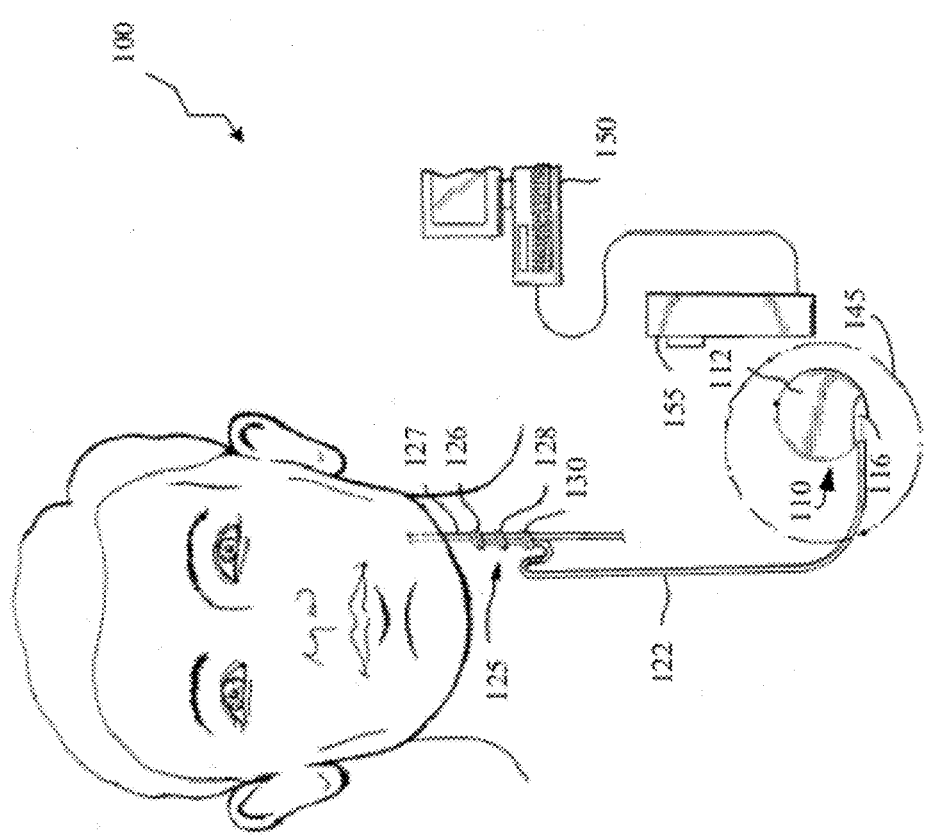

METHODS AND SYSTEMS FOR DETECTING EPILEPTIC EVENTS USING NONLINEAR ANALYSIS PARAMETERS

FIELD OF THE INVENTION

This invention relates generally to medical device systems and, more particularly, to medical device systems and methods capable of determining and, in some embodiments, treating an occurring or impending epilepsy event, for example an epileptic event.

DESCRIPTION OF THE RELATED ART

Many advancements have been made in treating diseases such as depression and epilepsy. Therapies using electrical signals for treating these diseases have been found to effective. Implantable medical devices have been effectively used to deliver therapeutic stimulation to various portions of the human body (e.g., the vagus nerve) for treating these diseases. As used herein, "stimulation," "neurostimulation," "stimulation signal," or "neurostimulation signal" refers to the application of an electrical, mechanical, magnetic, electromagnetic, photonic, audio, and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electromagnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a medical condition by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in neuro-plasticity or neurogenesis of brain tissue.

In some embodiments, electrical neurostimulation may be provided by implanting an electrical device, i.e., an implantable medical device (IMD), underneath the skin of a patient and delivering an electrical signal to a nerve such as a cranial nerve. Generally, electrical neurostimulation signals that perform neuromodulation are delivered by the IMD via one or more leads, although leadless neurostimulators have also been developed. The leads generally terminate at their distal ends in one or more electrodes, and the electrodes, in turn, are electrically coupled to tissue in the patient's body. For example, a number of electrodes may be attached to various points of a nerve or other tissue inside a human body for delivery of a neurostimulation signal.

While feedback stimulation (i.e., an electrical signal applied in response to a sensed body parameter such as heart rate) schemes have been proposed, conventional vagus nerve stimulation (VNS) usually involves non-feedback stimulation characterized by a number of parameters. Specifically, conventional vagus nerve stimulation usually involves a series of grouped electrical pulses defined by an "on-time" and an "off-time." Each sequence of pulses during an on-time may be referred to as a "pulse burst." The burst is followed by the off-time period in which no signals are applied to the nerve. During the on-time, electrical pulses of a defined electrical current (e.g., 0.5-2.0 milliamps) and pulse width (e.g., 0.25-1.0 milliseconds) are delivered at a defined frequency (e.g., 20-30 Hz) for the on-time duration, usually a specific number of seconds, e.g., 10-60 seconds. The pulse bursts are separated from one another by the off-time, (e.g., 30 seconds-5 minutes) in which no electrical signal is applied to the nerve. The on-time and off-time parameters together define a duty cycle, which is the ratio of the on-time to the combination of the on-time and off-time, and which describes the percentage of time that the electrical signal is applied to the nerve.

In conventional VNS, the on-time and off-time may be programmed to define an intermittent pattern in which a repeating series of electrical pulse bursts are generated and applied to a cranial nerve such as the vagus nerve. The off-time is provided to allow the nerve to recover from the stimulation of the pulse burst, and to conserve power. If the off-time is set at zero, the electrical signal in conventional VNS may provide continuous stimulation to the vagus nerve. Alternatively, the off time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in conventional VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-150 Hz (i.e., 20 pulses per second to 150 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Although neurostimulation has proven effective in the treatment of a number of medical conditions, it would be desirable to further enhance and optimize neurostimulation for this purpose. For example, it may be desirable to detect an occurring or impending epilepsy event. Such detection may be useful in monitoring the course of a patient's disease or the progress of his or her treatment thereof. Alternatively or in addition, such detection may be useful in warning the patient of an impending epilepsy event or alerting the patient, a physician, a caregiver, or a suitably programmed computer in order for that person or computer program to take action intended to reduce the likelihood, duration, or severity of the epilepsy event or impending epilepsy event, or to facilitate further medical treatment or intervention for the patient. Conventional VNS stimulation as described above does not detect occurring or impending epilepsy events.

SUMMARY OF THE INVENTION

In one aspect of the present invention, a method of detecting an epilepsy event in a patient is provided. In one embodiment, the method comprises receiving data relating to a beat sequence of the patient's heart; determining at least one regularity nonlinear analysis parameter associated with the beat sequence of the patient's heart and at least one predictability nonlinear analysis parameter associated with the beat sequence of the patient's heart; comparing the at least one of the at least one regularity nonlinear analysis parameter to a first threshold and the at least one predictability nonlinear analysis parameter to a second threshold; and providing an output indicative of at least one of an unstable brain state, a brain state indicative of an elevated probability of a seizure, a brain state indicative of an impending seizure, or a seizure based on the comparison.

In one aspect of the present invention, a method of detecting an epilepsy event in a patient is provided. In one embodiment, the method comprises receiving data relating to a beat sequence of the patient's heart; determining at least one regularity nonlinear analysis parameter associated with the beat sequence of the patient's heart; comparing at least one of the at least one regularity nonlinear analysis parameter to a first threshold; and providing an output indicative of at least one of an unstable brain state, a brain state indicative of an elevated probability of a seizure, a brain state indicative of an impending seizure, or a seizure based on the comparison.

In one aspect of the present invention, a method of detecting an epilepsy event in a patient is provided. In one embodiment, the method comprises receiving data relating to a beat sequence of the patient's heart; determining at least one predictability nonlinear analysis parameter associated with the beat sequence of the patient's heart; comparing the at least one predictability nonlinear analysis parameter to a second threshold; and providing an output indicative of at least one of an unstable brain state, a brain state indicative of an elevated probability of a seizure, a brain state indicative of an impending seizure, or a seizure based on the comparison.

In one aspect of the present invention, a method of detecting an epilepsy event is provided. In one embodiment, the method comprises receiving data relating to a beat sequence of the patient's heart; determining at least one nonlinear analysis parameter associated with the beat sequence of the patient's heart; comparing the nonlinear analysis parameter to a threshold; and providing an output indicative of at least one of an unstable brain state, a brain state indicative of an elevated probability of a seizure, a brain state indicative of an impending seizure, or a seizure based upon the comparing of the nonlinear analysis parameter to the threshold.

In another aspect of the present invention, a medical device for detecting an epilepsy event is provided. In one embodiment, the medical device comprises a sensing module adapted to receiving data relating to a beat sequence of the patient's heart; a nonlinear analysis parameter processing module adapted to determining at least one nonlinear analysis parameter associated with the beat sequence of the patient's heart, and adapted to compare the nonlinear analysis parameter to a threshold; and a communication unit adapted to provide an output indicative of at least one of an unstable brain state, a brain state indicative of an elevated probability of a seizure, a brain state indicative of an impending seizure, or a seizure based upon the comparing of the nonlinear analysis parameter to the threshold. In one embodiment, the medical device comprises an implantable medical device.

In yet another aspect of the present invention, a computer readable program storage device is provided that is encoded with instructions that, when executed by a computer, perform the method described above.

In one embodiment, a medical device system is provided that comprises the medical device described above.

BRIEF DESCRIPTION OF THE DRAWINGS

The invention may be understood by reference to the following description taken in conjunction with the accompanying drawings, in which like reference numerals identify like elements, and in which:

FIG. 1A provides a stylized diagram of an implantable medical device implanted into a patient's body for providing a therapeutic electrical signal to a neural structure of the patient's body, in accordance with one illustrative embodiment of the present invention;

Figure 1B:
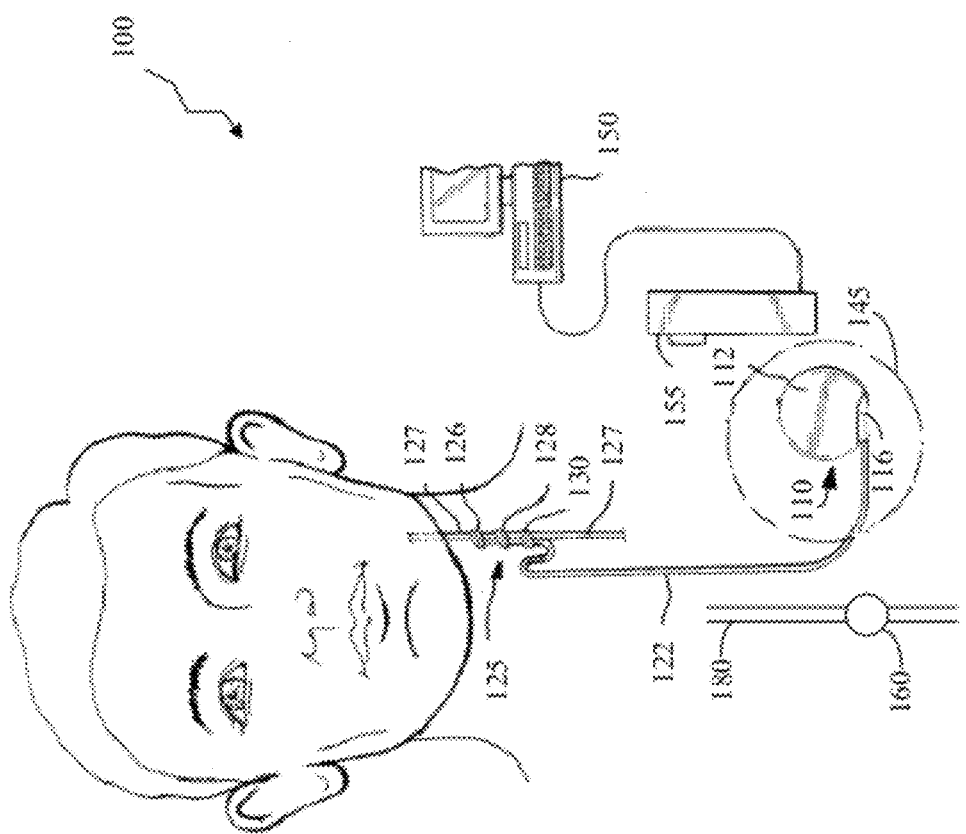
FIG. 1B provides a stylized diagram of an implantable medical device implanted into a patient's body for providing a therapeutic electrical signal to a neural structure of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

In one embodiment, the present invention provides a method of detecting an epilepsy event. The epilepsy event can be, for example, at least one of an unstable brain state, a brain state indicative of an elevated probability of a seizure, a brain state indicative of an impending seizure, or a seizure, among others.

In one embodiment, the method comprises receiving data relating to a beat sequence of the patient's heart; determining at least one nonlinear analysis parameter associated with the beat sequence of the patient's heart; comparing the nonlinear analysis parameter to at least one threshold; and providing an output indicative of at least one of an unstable brain state, a brain state indicative of an elevated probability of a seizure, a brain state indicative of an impending seizure, or a seizure based upon the comparing of the nonlinear analysis parameter to the at least one threshold.

In one embodiment, the present invention provides a method of taking action responsive to an epilepsy event in a patient, comprising receiving data relating to a beat sequence of the patient's heart; determining at least one nonlinear analysis parameter associated with the beat sequence of the patient's heart; comparing the nonlinear analysis parameter to at least one threshold; and taking a responsive action selected from warning, logging the time of the seizure, computing and storing one or more seizure severity indices, and treating the epilepsy event based upon the comparing of the nonlinear analysis parameter to the at least one threshold.

In one embodiment, treating the epilepsy event comprises cranial nerve stimulation. Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain (including neuropathic pain and fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, the precise stimulation parameters that would modulate particular pathways relevant to a particular disorder generally cannot be predicted.

In some embodiments, electrical neurostimulation may be provided by implanting an electrical device underneath the skin of a patient and delivering an electrical signal to a nerve such as a cranial nerve. In another alternative embodiment, the signal may be generated by an external pulse generator outside the patient's body, coupled by an RF or wireless link to an implanted electrode.

The data relating to a beat sequence of the patient's heart can be gathered by any of a number of techniques. For example, data relating to a beat sequence may be gathered by an electrocardiogram (ECG) device, such as the CardioBelt ECG acquisition system (offered by Monebo Technologies, Inc., Austin, Tex.). In one embodiment, the data relating to the beat sequence may be related to the R-waves of the beat sequence, such as a time series of R-waves or a series of R-R intervals. Those skilled in the art having benefit of the present disclosure would appreciate that other time series of cardiac waves and/or their fiducial points (e.g., P waves, T waves, etc.) may be used and still remain within the spirit and scope of the present invention.

Data relating to R-waves may be gathered by an ECG device or, in one embodiment, by a vagus nerve stimulator, such as described in U.S. patent application Ser. No. 12/258, 019, filed Oct. 24, 2008, which is hereby incorporated by reference herein.

Receiving the data relating to the beat sequence of the patient's heart may comprise sensing a time of beat sequence of a patient's heart and generating a time series data stream from said time of the beat sequence. In a further embodiment, receiving the data relating to the beat sequence of the patient's heart may comprise receiving a series of R-R intervals, and generating the time series data stream may comprise sensing a plurality of R peaks from the R-R intervals and using the R peaks for providing a time stamp to generate the time series data stream based upon the time stamp.

Based upon the R-R intervals time series, many periodic and non-periodic parameters may be evaluated using statistical, geometrical, spectral analysis and linear dynamic methods. However, in spite of promising results in the detection of seizures, the methods referred to in the previous sentence lack specificity. In other words, they yield an unacceptably high rate of falsely detected seizure events.

For example, it is known that heart rate (HR) increases in 98% of seizure events and may serve as a reliable indicator of a seizure. However, the HR increase may occur during normal neurological activity (e.g., a heart rate change induced by exercise or intense emotion, among others). Consequently, the HR increase is a good indicator of a seizure in terms of sensitivity (i.e., a low rate of false negative seizure detections) but a very poor indicator in terms of specificity (i.e., rate of false positives).

Figure 12:
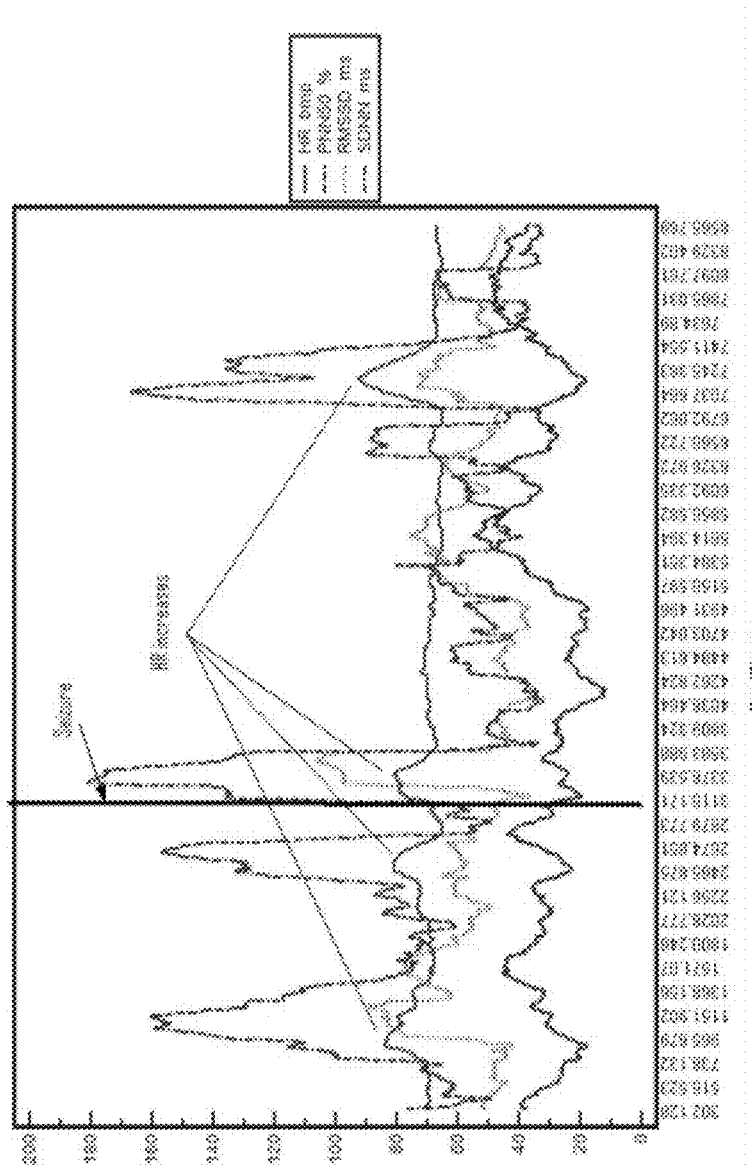
FIG. 12 illustrates a time series of observed values for statistical parameters related to heart rate variability (Percentage of differences between adjacent NN intervals that are >50 msec (PNN50), Standard Deviation Normal to Normal R-R intervals (SDNN), and Root Mean Square Successive Difference (RMSSD)) over two and half hours of monitoring with detected and marked seizure events, as well as heart rate increases not contemporaneous with any seizure event, in the same patient as FIG. 9.
Figure 13:
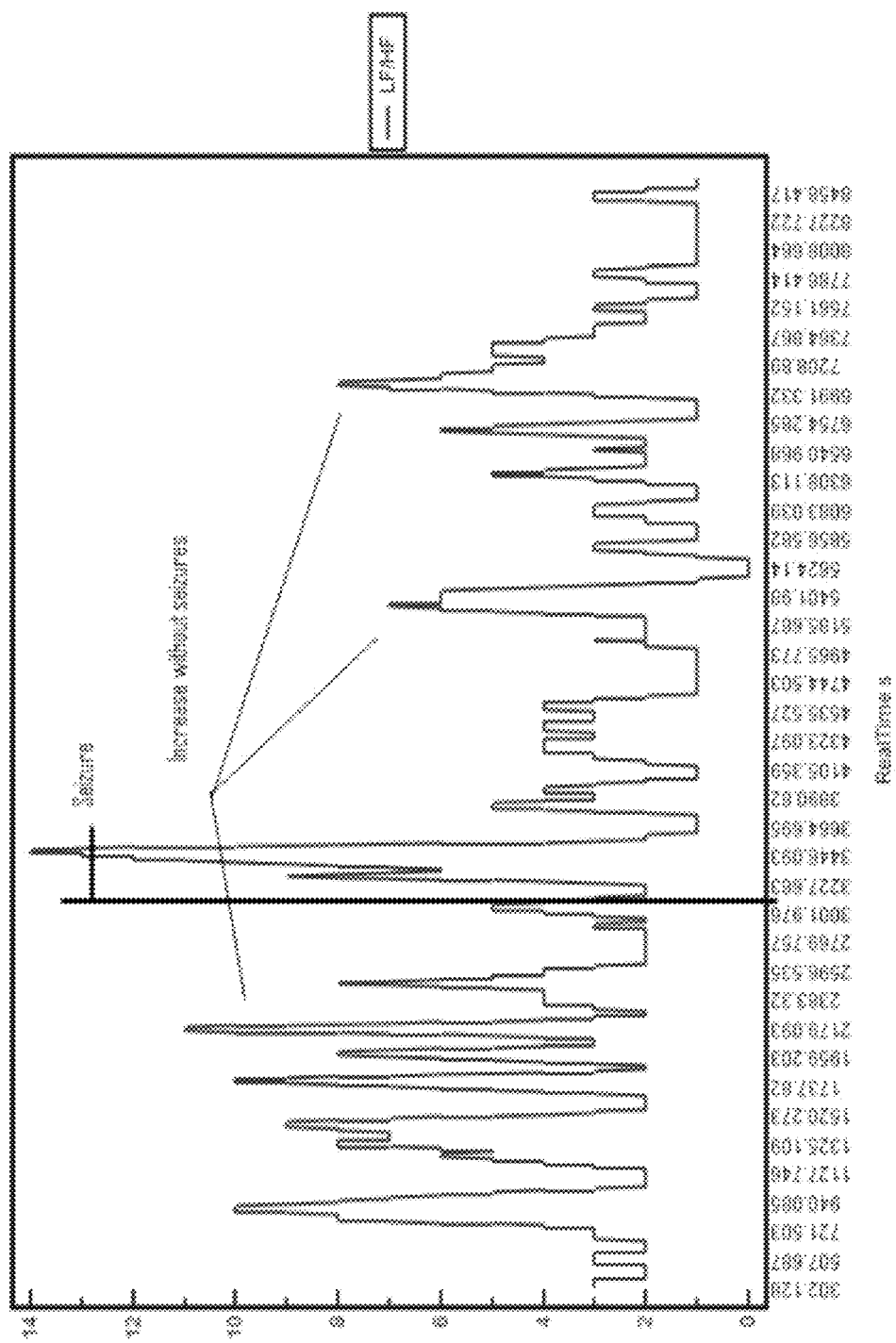
FIG. 13 illustrates a time series of observed values for a spectral parameter related to heart rate variability (low frequency (LF) to high frequency (HF) ratio) over two and half hours of monitoring with a detected and marked seizure event, as well as increases in the LF/HF ratio not contemporaneous with any seizure event, in the same patient as FIG. 9.

The same results have been seen using other statistical Heart Rate Variability (HRV) parameters such as Standard Deviation Normal to Normal R-R intervals (SDNN), Root Mean Square Successive Difference (RMSSD), Coefficient of Variance (CV) and Percentage of differences between adjacent NN intervals that are >50 msec (PNN50) which have high negative or positive correlation coefficients with HR. FIG. 12 shows significant increase/decrease of all above parameters at a time near a seizure, but also at three other times without seizures, yielding 3 false detections or a false positive rate of 75%. Also, the significant increases/decreases at a time near a seizure takes place up to roughly 240 sec (4 min) after seizure onset Many spectral analysis HRV parameters also lack specificity. As an example, FIG. 13 illustrates numerous large increases in the low frequency (LF) to high frequency (HF) ratio at times not associated with seizures (false positives). The only large increase taking place at any time near a seizure takes place roughly 300 sec (5 min) after seizure onset.

Besides the lack of specificity, statistical and spectral analysis parameters significantly change a few minutes after a seizure, which makes them impractical for the timely intervention and/or warning of seizures. See FIGS. 12-13.

In contrast to statistical and spectral analysis measures, the evaluation of nonlinear analysis parameters, and especially the measurement of entropy and predictability of non-periodic oscillations of R-R time series, can be suitable for prediction and/or detection of seizure events providing satisfactory level of both sensitivity and specificity in a timely manner, such as at the onset of the seizure event.

From the time series data, at least one nonlinear analysis parameter associated with the beat sequence of the patient's heart can be determined. A "nonlinear analysis parameter" is used herein to refer to a nonlinear dynamics parameter which classifies complex, non-periodic oscillations of a time series of R-R intervals. In certain embodiments, a nonlinear analysis parameter may be referred to as a "chaos parameter."

Exemplary nonlinear analysis parameters include a group of parameters which measure the entropy of a complex system, for example approximate entropy (ApEn), fuzzy entropy (FuzzyEn), and sample entropy (SampEn). ApEn, FuzzyEn, and SampEn measure a statistical regularity of a nonlinear time series and reflect a complexity of non-periodic oscillations of HRV. Though not to be bound by theory, greater regularity means lesser complexity, and hence lesser adaptability and functionality.

Another group of nonlinear analysis parameters includes parameters measuring the predictability of a complex system. As an example, the similarity of distribution of math expectancy (SOD), a probability parameter which measures predictability of non-periodic oscillations of HRV. Though not to be bound by theory, higher predictability of a system means lesser flexibility and functionality.

There are other versions of entropy (regularity) and predictability parameters adapted to specific needs, depending on what time-series signal is desired to be classified, the available duration of the time series, static versus dynamic evaluation, the minimal/maximal size of sliding windows for parameter calculation, and the sliding window step size, among others. For example, recently introduced FuzzyEn (Measuring complexity using FuzzyEn, ApEn, and SampEn Weiting Chen, Jun Zhuang, Wangxin Yu, Zhizhong Wang Medical engineering & physics 1 Jan. 2009 (volume 31 issue 1 Pages 61-68 DOI: 10.1016/j.medengphy.2008.04.005).

In one embodiment, the regularity nonlinear analysis parameter is SampEn and the predictability nonlinear analysis parameter is SOD, for analysis of the non-periodic oscillations of R-R intervals time series for prediction and detection of seizure events.

Sample entropy (SampEN) is the negative natural logarithm of the conditional probability that two sequences similar for m points remain similar at the $(m+1)^{th}$ point, wherein self-matches are not included in calculating the probability. Sample entropy is defined in terms of m, r, and N, wherein m is the length of the sequences to be compared, r is the tolerance for accepting matches, and N is the length of the time series.

Specifically, in one embodiment, if Bm(r) (Am(r)) is an estimate of the probability that two sequences will match for m(m+1) points, with Ai being an m+1 counterpart of Bi:

$$B^m(r) = \frac{1}{N-m} \cdot \sum_{i=1}^{N-m} \frac{B_i - 1}{N-m-1},$$

$$A^m(r) = \frac{1}{N-m} \cdot \sum_{i=1}^{N-m} \frac{A_i - 1}{N-m-1}$$

then sample entropy is estimated as:

$$SampEn(m, r, N) = -\ln\left(\frac{A^m(r)}{B^m(r)}\right)$$

T. Loncar-Turukalo, S. Milosavljevic, O Sarenac, N. Japundzic-Zigon, D. Bajic: "Entropy and Gaussianity—Measures of Deterministic Dynamics of Heart Rate and Blood Pressure Signals in Rats", Acta Polytechnica Hungarica, Vol. 5, No. 1, 2008, pp 121-133, ISSN 1785-8860.

Sample entropy can be considered a measure of the regularity of a system. The lower value of SampEn reflects the higher level of regularity. The electrophysiological rhythms are irregular by nature. The high level of regularity may be a manifestation of a pathological condition.

Similarity of distribution (SOD) is a measurement of the autocorrelation of a distribution of a time series of data points.

SOD shows changes in the width of the distribution and the stability of the distribution over time. Zochowski M., Winkowska-Nowak K., Nowak A., Karpinski G., & Budaj A. (1997). Autocorrelations of R-R distributions as a measure of heart rate variability. *Physical Review E,* 56, 3725-2727.

Specifically, in one embodiment, the time series to be analyzed is divided into a sequence of time periods which are moved by s with respect to each other and a probability distribution for the data points (in one embodiment, R-R intervals) is determined. SOD (represented by the variable A(s)) is then:

$$A(s) = \sum_{i=1}^{h} p_i(t)p_i(t+s)$$

where h is the number of cells in the histogram of the probability distribution, t is the starting time point of the window, and $p_i(t)$ is the $i^{th}$ cell of the histogram. SOD will vary from 0 to 1. As it approaches 0, it suggests the probability distributions are very wide or the data sets do not overlap. As it approaches 1, it suggests the probability distributions have a high degree of overlap. SOD can be considered a measure of the stability and predictability of the system at a given time. Though not to be bound by theory, the higher value reflects the higher stability and predictability of the system. The high level of stability and predictability may indicate a pathological state.

Both SampEN and SOD can be calculated effectively from relatively short time windows (up to 10 beats) and SOD is fairly tolerant of noise in the time series data signal.

In addition to the nonlinear analysis parameters described above, other nonlinear analysis parameters exist, for example chaos parameters such as largest Lyapunov exponent, Fractal Dimension by Dispersion Analysis (FDDA), and Detrended Fluctuation Analysis (DFA). However, these parameters are less suitable for applications provided by embodiments of the present invention because they require at least about 300 seconds of time series data for valid results. Moreover, some of these parameters lack sensitivity (e.g., the largest Lyapunov exponent) or specificity (e.g., FDDA and DFA).

Alternatively or in addition, many of the other nonlinear analysis parameters may have a low specificity for detecting an epilepsy event, i.e., their use in methods of detecting epilepsy events may yield many false positives.

One advantage of the use of SampEN and SOD to detect seizures is that these two nonlinear analysis parameters have no statistically significant correlation between each other. Further, SOD has no statistically significant correlation with HR, as shown in the following table:

|  |  | HR bmp | SampEn | SODmax |
|---|---|---|---|---|
| HR bmp | Correlation Coefficient |  | −0.827 | 0.068 |
|  | Significance Level P |  | 0.0000 | 0.03492 |
|  | n |  | 963 | 963 |
| SampEn | Correlation Coefficient | −0.827 |  | −0.109 |
|  | Significance Level P | 0.0000 |  | 0.0007244 |
|  | n | 963 |  | 963 |
| SODmax | Correlation Coefficient | 0.068 | −0.109 |  |
|  | Significance Level P | 0.03492 | 0.0007244 |  |
|  | n | 963 | 963 |  |

Pearson correlation coefficient

Also, SampEN and SOD reflect different specifics of the R-R time series. Therefore, use of both these parameters (and like non-linear measures of regularity and predictability) yield higher sensitivity and specificity in prediction and detection of seizure events.

Once determined, the nonlinear analysis parameter may be compared to one or more thresholds. The threshold can be established by a physician based on one or more of the particular nonlinear analysis parameter under consideration, the patient's age, the patient's sex, the condition of the patient's heart, the severity of the patient's medical disorder, and/or other parameters. For example, if the nonlinear analysis parameter is SampEN, the lower threshold may be 0.25. For another example, if the nonlinear analysis parameter is SOD, the upper threshold may be 0.75. For another example, the nonlinear analysis parameter may be SOD-SampEN and the threshold may be 0.5.

Based on the comparison between the nonlinear analysis parameter and the threshold, a responsive action may be taken selected from warning, logging the time of a seizure, computing and storing one or more seizure severity indices, and treating the epilepsy event.

A warning may be given as a warning tone or light implemented by a medical device or a device adapted to receive indications of an epilepsy event; as an automated email, text message, telephone call, or video message sent from a medical device or a unit in communication with a medical device to the patient's cellular telephone, PDA, computer, television, etc. Such a warning may allow the patient or his or her caregivers to take measures protective of patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc.

The time may be logged by receiving an indication of the current time and associating the indication of the current time with an indication of the epilepsy event.

Seizure severity indices may be calculated and stored by appropriate techniques and apparatus.

The epilepsy event may be treated by appropriate techniques, such as those discussed below.

Returning to the comparison, for example, if the nonlinear analysis parameter is (SOD−SampEN), i.e., the SOD value at a particular time point minus the SampEN value at the same time point, and the threshold is 0.2, and if the (SOD−SampEN) value is above 0.2 but below 0.6 a warning about imminent seizure may be given, the time to the expected seizure may be logged, one or more prediction indices may be calculated and stored, the preventive treatment may be provided, or two or more thereof. For another example, if the nonlinear analysis parameter is (SOD−SampEn) and the threshold is 0.6, and if the (SOD−SampEn) value is above the threshold, an alarm may be given, the time may be logged, one or more seizure severity indices may be calculated and stored, the epilepsy event may be treated, or two or more thereof. The term "treatment" may refer to intervening in an ongoing epilepsy event in an effort to reduce the impact or intensity of the epilepsy event, or it may refer to an attempt to reduce the impact or intensity of a seizure, or abort the seizure entirely, at a time before a seizure has begun. Reducing the intensity of an epilepsy event may include incrementally reducing the intensity, substantially reducing the intensity, or substantially eliminating the intensity of the epilepsy event.

The treatment may be one or more treatments known in the art. In one embodiment, the treatment comprises at least one of applying an electrical signal to a neural structure of a patient; delivering a drug to a patient; or cooling a neural structure of a patient. When the treatment comprises applying an electrical signal to a portion of a neural structure of a patient, the neural structure may be at least one of a portion of a brain structure of the patient, a portion of a cranial nerve of a patient, a portion of a spinal cord of a patient, a portion of a sympathetic nerve structure of the patient, a portion of a parasympathetic nerve structure of the patient, and/or a portion of a peripheral nerve of the patient.

A plurality of thresholds may be provided, referring to either any combination of a plurality of nonlinear analysis parameters, a plurality of time periods, or a plurality of conditional events. For example, a physician may require both a SampEN value below 0.25 and a SOD value above 0.75 at the same time for the device to declare an epileptic event; or an SOD-SampEN value of 0.5 to remain for at least 1-10 seconds for the device to declare an epileptic event; or a SampEN value below about 0.25 from 1-10 seconds after a SOD value above about 0.75 for the device to declare an epileptic event, among others.

Though not intended to be bound by theory, in certain circumstances, one or more nonlinear analysis parameters may exceed or fall below a threshold at a time before the onset of an epileptic event, wherein onset is determined by electroencephalography, observation by a physician or knowledgeable layman, or both. The time before onset may range from a few seconds up to 15-20 minutes. As such, certain embodiments of the method may be considered to yield a prediction of an epileptic event. It should be noted that the prediction may sometimes be a false positive; however, depending on a physician's judgment, his or her understanding of the devices in use, and the patient's condition, a certain amount of false positives may be tolerable.

The above method can be performed alone. In one embodiment, the above method can be performed in combination with a continuous or open-loop therapy for epilepsy. In one embodiment, the above method is performed to take action in response to the detection of an epilepsy event, and at all or most other times, a chronic therapy signal is applied to a target structure in the patient's body. In one embodiment, the target structure is a cranial nerve, such as the vagus nerve.

Although not so limited, a system capable of implementing embodiments of the present invention is described below. FIG. 1A depicts a stylized implantable medical system (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the vagus nerve 127 by a spiral anchoring tether 130 such as that disclosed in U.S. Pat. No. 4,979, 511 issued Dec. 25, 1990 to Reese S. Terry, Jr. Lead assembly 122 may be secured, while retaining the ability to flex with movement of the chest and neck, by a suture connection to nearby tissue (not shown).

In alternative embodiments, the electrode assembly 125 may comprise temperature sensing elements and/or heart rate sensor elements. Other sensors for other body parameters may also be employed. Both passive and active stimulation may be combined or delivered by a single IMD according to the present invention. Either or both modes may be appropriate to treat a specific patient under observation.

Figure 1C:
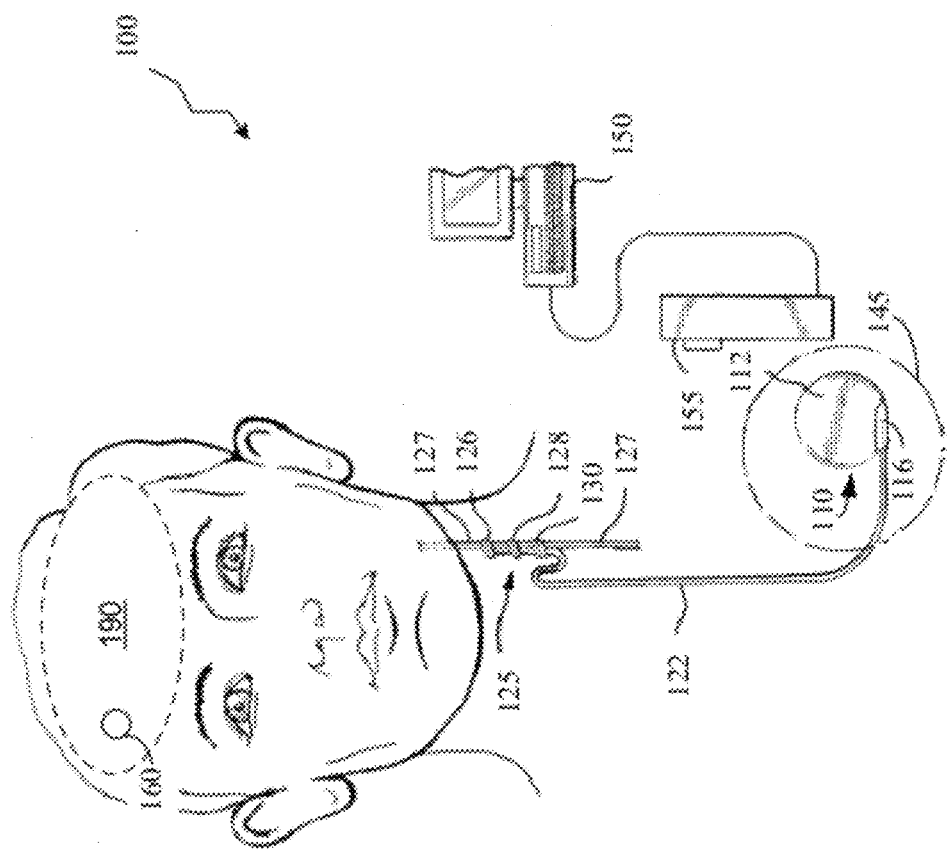
FIG. 1C provides a stylized diagram of an implantable medical device implanted into a patient's body for providing a therapeutic electrical signal to a neural structure of the patient's body, in accordance with one illustrative embodiment of the present invention.

In alternative embodiments, the implantable medical device system further comprises an electrical stimulator comprising an electrode 160 (not to scale) adapted to be coupled to the spinal cord 180 (FIG. 1B) or to a region of the brain 190 (FIG. 1C). The physician can select precise locations for coupling to the spinal cord 180 or brain 190 based on his or her observations of the patient's medical condition, among other values. In various embodiments, the implantable medical device system may comprise one, two, or three of the IMD 100, the spinal cord stimulator, and the brain stimulator.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

Turning now to FIG. 2, a block diagram depiction of a medical device 200 is provided, in accordance with one illustrative embodiment of the present invention.

In some embodiments, the medical device 200 may be implantable (such as implantable electrical signal generator 110 from FIG. 1), while in other embodiments the medical device 200 may be completely external to the body of the patient.

Figure 2A:
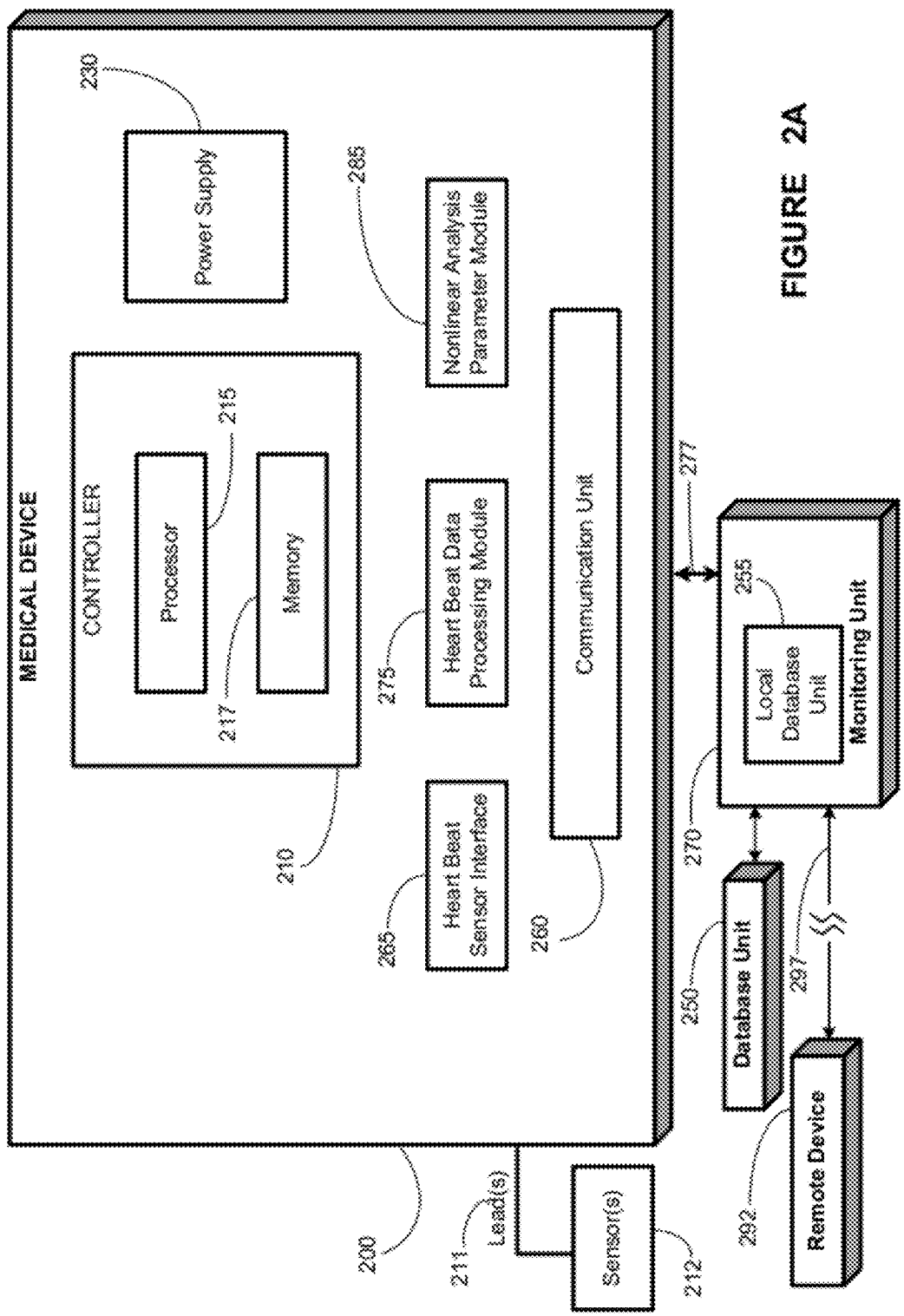
FIG. 2 is a block diagram of a medical device system that includes an implantable medical device and an external device, in accordance with one illustrative embodiment of the present invention.

The medical device 200 (such as generator 110 from FIG. 1) may comprise a controller 210 capable of controlling various aspects of the operation of the medical device 200. The controller 210 is capable of receiving internal data or external data, and in one embodiment, is capable of causing a stimulation unit 220 (FIG. 2B) to generate and deliver an electrical signal to target tissues of the patient's body for treating a medical condition. For example, the controller 210 may receive manual instructions from an operator externally, or may cause the electrical signal to be generated and delivered based on internal calculations and programming. In other embodiments, the medical device 200 does not comprise a stimulation unit 220 (FIG. 2A). In either embodiment, the controller 210 is capable of affecting substantially all functions of the medical device 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

Figure 2B:
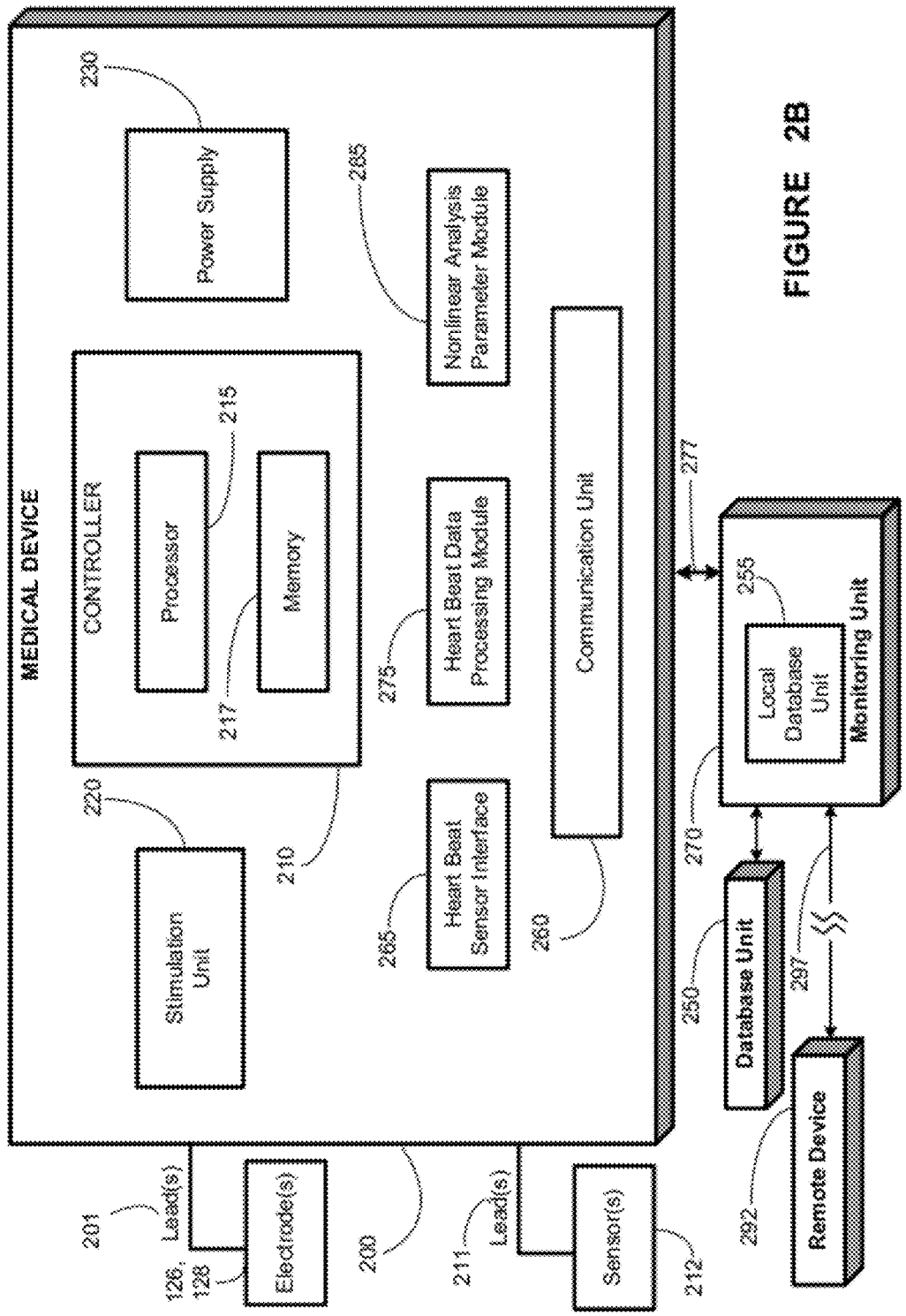

As stated above, in one embodiment, the medical device 200 may also comprise a stimulation unit 220 capable of generating and delivering electrical signals to one or more electrodes 126, 128 via leads 201 (FIG. 2B). A lead assembly such as lead assembly 122 (FIG. 1) may be coupled to the medical device 200. Therapy may be delivered to the leads 201 comprising the lead assembly 122 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue. The stimulation unit 220 is capable of delivering electrical signals over the leads 201 comprising the lead assembly 122. As should be apparent, in certain embodiments, the medical device 200 does not comprise a stimulation unit 220, lead assembly 122, or leads 201.

In other embodiments, a lead 201 is operatively coupled to an electrode, wherein the electrode is adapted to couple to at least one of a portion of a brain structure of the patient, a cranial nerve of a patient, a spinal cord of a patient, a sympathetic nerve structure of the patient, or a peripheral nerve of the patient.

The medical device 200 may also comprise a power supply 230. The power supply 230 may comprise a battery, voltage regulators, capacitors, etc., to provide power for the operation of the medical device 200, including delivering the therapeutic electrical signal. The power supply 230 comprises a power source that in some embodiments may be rechargeable. In other embodiments, a non-rechargeable power source may be used. The power supply 230 provides power for the operation of the medical device 200, including electronic operations and the electrical signal generation and delivery functions. The power supply 230 may comprise a lithium/thionyl chloride cell or a lithium/carbon monofluoride (LiCFx) cell if the medical device 200 is implantable, or may comprise conventional watch or 9V batteries for external (i.e., non-implantable) embodiments. Other battery types known in the art of medical devices may also be used.

The medical device 200 may also comprise a communication unit 260 capable of facilitating communications between the medical device 200 and various devices. In particular, the communication unit 260 is capable of providing transmission and reception of electronic signals to and from an monitoring unit 270, such as a handheld computer or PDA that can communicate with the medical device 200 wirelessly or by cable. The communication unit 260 may include hardware, software, firmware, or any combination thereof.

The medical device 200 may also comprise one or more sensor(s) 212 coupled via sensor lead(s) 211 to the medical device 200. The sensor(s) 212 are capable of receiving signals related to a physiological parameter, such as the patient's heart beat, and delivering the signals to the medical device 200. In one embodiment, the sensor(s) 212 may be the same as implanted electrode(s) 126, 128 (FIG. 1). In other embodiments, the sensor(s) 212 are separate structures that may be placed on the patient's skin, such as over the patient's heart or elsewhere on the patient's torso.

In one embodiment, the medical device 200 may comprise a heart beat sensor interface 265 that is capable of receiving signals related to the patient's heart beat from the sensor(s) 212. The heart beat sensor interface 265 may be capable of performing any necessary or suitable amplifying, filtering, and performing analog-to-digital (A/D) conversions to prepare the signals for downstream processing. The heart beat sensor interface, in one embodiment, may comprise software module(s) that are capable of performing various interface functions, filtering functions, etc., to process heart rate signals. In another embodiment the heartbeat sensor interface 265 may comprise hardware circuitry that is capable of performing these functions. In yet another embodiment, the heartbeat sensor interface 265 may comprise hardware, firmware, software and/or any combination thereof. A more detailed illustration of the heartbeat sensor interface 265 is provided in FIG. 3A and accompanying description below.

The heartbeat sensor interface 265 is capable of receiving heartbeat signals and providing the signal to a heart rate data processing module 275. Based upon the signals processed by the heart beat sensor interface 265, a heart beat data processing module 275 may determine various properties of the patient's heart beat time series and store such properties or forward them on for further processing/analysis. In one embodiment, the heart rate data processing module 275 is capable of processing the heart beat into various components such that information relating to an epilepsy event is provided. For example, the heart rate data processing module 275 is capable of processing the heart beat signals into a form such that various nonlinear analysis parameters described herein, which are indicative of an acute physiological event, may be determined. For example, parameters such as SampEN and SOD that may be indicative of an increased risk of an epileptic seizure may be determined by the heart beat data processing module 275. Further description of the heart rate data processing module 275 is provided in FIG. 3B and accompanying description below.

Moreover, the medical device 200 may also comprise a nonlinear analysis module 285. The nonlinear analysis module 285 is capable of performing chaos analysis of the data derived from the heart beat signal. Further description of the nonlinear analysis module 285 is provided in FIG. 4 and accompanying description below.

In addition to components of the medical device 200 described above, an implantable medical system may comprise a storage unit to store an indication of at least one of seizure or an increased risk of a seizure. The storage unit may be the memory 217 of the medical device 200, another storage unit of the medical device 200, or an external database, such as the local database unit 255 or a remote database unit 250. The medical device 200 may communicate the indication via the communications unit 260. Alternatively or in addition to an external database, the medical device 200 may be adapted to communicate the indication to at least one of a patient, a caregiver, or a healthcare provider.

In various embodiments, one or more of the units or modules described above may be located in an monitoring unit 270 or a remote device 292, with communications between that unit or module and a unit or module located in the medical device 200 taking place via communication unit 260. For example, in one embodiment, the nonlinear analysis module 285 may be external to the medical device 200, e.g., in a monitoring unit 270. Locating the nonlinear analysis module 285 outside the medical device 200 may be advantageous if the nonlinear analysis parameter calculation is computationally intensive, in order to reduce energy expenditure and heat generation in the medical device 200 or to expedite calculation of the at least one nonlinear analysis parameter.

The monitoring unit 270 may be a device that is capable of transmitting and receiving data to and from the medical device 200. In one embodiment, the monitoring unit 270 is a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less interactive communication with the medical device 200 than another monitoring unit 270 controlled by a healthcare provider. Whether controlled by the patient or by a healthcare provider, the monitoring unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 270 may download various parameters and program software into the medical device 200 for programming the operation of the medical device, and may also receive and upload various status conditions and other data from the medical device 200. Communications between the monitoring unit 270 and the communication unit 260 in the medical device 200 may occur via a wireless or other type of communication, represented generally by line 277 in FIG. 2. This may occur using, e.g., wand 155 (FIG. 1) to communicate by RF energy with an implantable signal generator 110. Alternatively, the wand may be omitted in some systems, e.g., systems in which the MD 200 is non-implantable, or implantable systems in which monitoring unit 270 and MD 200 operate in the MICS bandwidths.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting thresholds for one or more detection parameters) using the monitoring unit 270, which may include obtaining and/or analyzing data from the medical device 200 and/or data from the database unit 250 and/or the local database unit 255. The database unit 250 and/or the local database unit 255 may store various patient data.

One or more of the blocks illustrated in the block diagram of the medical device 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

The medical device system of one embodiment of the present invention provides for software module(s) that are capable of acquiring, storing, and processing various forms of data, such as patient data/parameters (e.g., physiological data, side-effects data, such as heart rate, breathing rate, brain-activity parameters, disease progression or regression data, quality of life data, etc.) and therapy parameter data. Therapy parameters may include, but are not limited to, electrical signal parameters that define therapeutic electrical signals delivered by the medical device in response to the detection of an epilepsy event, medication parameters and/or any other therapeutic treatment parameter. In an alternative embodiment, the term "therapy parameters" may refer to electrical signal parameters defining the therapeutic electrical signals delivered by the medical device. Therapy parameters for a therapeutic electrical signal may also include, but are not limited to, a current amplitude, a pulse width, a frequency, an on-time, an off-time, etc.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode may be coupled to either or both vagus nerves or a branch of either or both vagus nerves. The term "operatively" coupled may include directly or indirectly coupling. Each of the nerves in this embodiment or others involving two or more cranial nerves may be stimulated according to particular activation modalities that may be independent between the two nerves.

Returning to systems for providing cranial nerve stimulation, such as that shown in FIG. 1, and as stated above, alternatively or in addition to a responsive treatment, if any, cranial nerve stimulation may be provided on a continuous basis to alleviate chronic aspects of the patient's medical disorder. Where cranial nerve stimulation is provided based solely on programmed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually-triggered stimulation, in which the patient manually causes the activation of a pulse burst outside of the programmed on-time/off-time cycle. The patient may manually activate an implantable signal generator 110 to stimulate the cranial nerve, such as vagus nerve 127, to treat an acute episode of a medical condition, e.g., a seizure. The patient may also be permitted to alter the intensity of the signals applied to the cranial nerve within limits established by the physician.

Patient activation of an medical device 100 may involve use of an external control magnet for operating a reed switch in an implanted device, for example. Certain other techniques of manual and automatic activation of implantable medical devices are disclosed in U.S. Pat. No. 5,304,206 to Baker, Jr., et al. ("the '206 patent"). According to the '206 patent, means for manually activating or deactivating the electrical signal generator 110 may include a sensor such as piezoelectric element mounted to the inner surface of the generator case and adapted to detect light taps by the patient on the implant site. One or more taps applied in fast sequence to the skin above the location of the electrical signal generator 110 in the patient's body may be programmed into the implanted medical device 100 as a signal for intensification of the electrical signal. Two taps spaced apart by a slightly longer duration of time may be programmed into the medical device 100 to indicate a desire to de-intensify the electrical signal. The patient may be given limited control over operation of the device to an extent which may be determined by the program or entered by the attending physician. The patient may also activate the medical device 100 using other suitable techniques or apparatus.

In one embodiment, the medical device 200 may also be capable of detecting a manual input from the patient. The manual input may include a magnetic signal input, a tap input, a wireless data input to the medical device 200, etc.

Figure 3A:
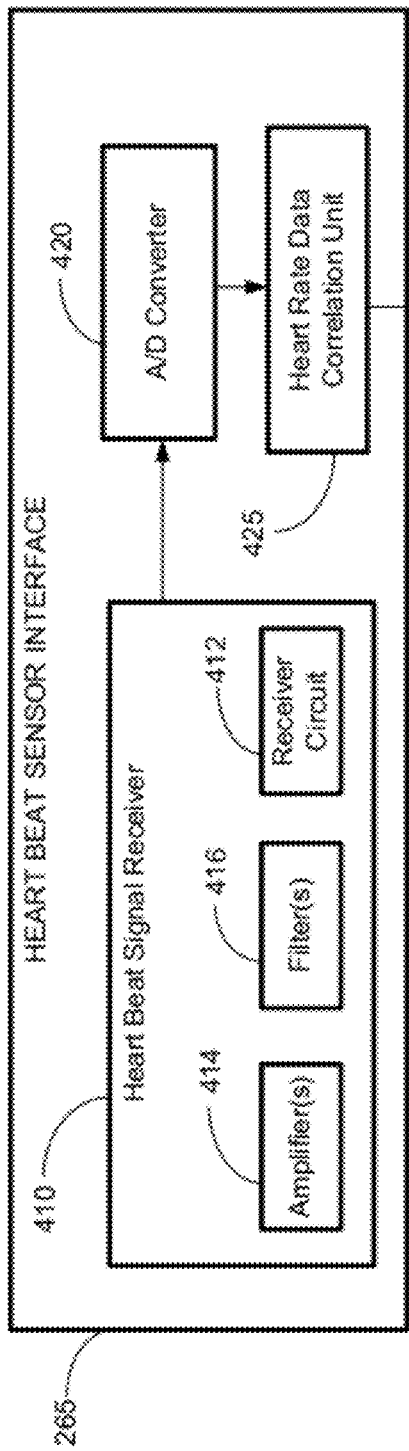
FIG. 3A is a stylized block diagram of a heart beat sensor interface of a medical device, in accordance with one illustrative embodiment of the present invention.

Turning now to FIG. 3A, a more detailed stylized depiction of the heart beat sensor interface 265 of FIG. 2, in accordance with one illustrative embodiment of the present invention is depicted. In one embodiment, the heart beat sensor interface 265 comprises a heart rate signal receiver 410, an analog-to-digital converter (A/D Converter) 420, and a heart rate data correlation unit 425. The heart rate signal receiver 410 is capable of receiving the signals from the sensor(s) 212 via receiver circuit 412. The signal that is received by the receiver circuit 412 is processed and filtered to enable the data to be further analyzed and/or processed for detection of an epilepsy event.

The heart rate signal receiver 410 may comprise amplifier(s) 414 and filter(s) 416. The amplifiers 414 are capable of buffering and amplifying the input signals received by the receiver circuit 412. In many cases, the heart beat signal may be attenuated and may be characterized by significantly low amplitude responses and signal noise. The amplifier(s) 414 are capable of buffering (amplification by unity) and amplifying the signals for further processing. In one embodiment, the amplifier 414 may comprise op amp circuit(s), digital amplifier(s), buffer amplifiers, and/or the like.

The heart beat signal receiver 410 may also comprise one or more filters 416. The filters 416 may comprise analog filter(s), digital filter(s), filters implemented by digital signal processing (DSP) means or methods, etc. The amplified and buffered heart beat signal may be filtered to remove various noise signals residing on the heart beat signal. The filter 416, for example, is capable of filtering out various noise signals caused by external magnetic fields, electrical fields, noise resulting from physiological activity, etc. Filtering, signal noise due to breathing or other signals produced by the patient's body may be filtered.

The heart beat signal receiver 410 provides amplified, filtered signals to the A/D converter 420. The A/D converter 420 performs an analog-to-digital conversion for further processing of the heart beat signal. The A/D converter 420 may be one type of a plurality of converter types with various accuracies, such as an 8-bit converter, a 12-bit converter, a 24-bit converter, a 32-bit converter, a 64-bit converter, a 128-bit converter, a 256-bit converter, etc. The converted digital signal is then provided to a heart rate data correlation unit 425. In an alternative embodiment, the A/D conversion may be performed prior to filtering or signal processing of the heart beat signal. The converted digital signal is then provided to a heart rate data correlation unit 425.

The heart rate data correlation unit 425 is capable of organizing, correlating, stacking, and otherwise processing the digitized, buffered, and filtered heart rate data. The heart rate correlation unit 425 is capable of correlating and organizing the digitized heart rate signal. The correlation unit 425 may correlate various time stamps with the heart beat signal to provide a time of beat sequence of the patient's heart. Further, the heart rate data correlation unit 425 is capable of correlating various physiological events to the heart beat data. The digital signals issuing from the heart rate data correlation unit 425 may then be forwarded to the heart beat data processing module 275.

Figure 3B:
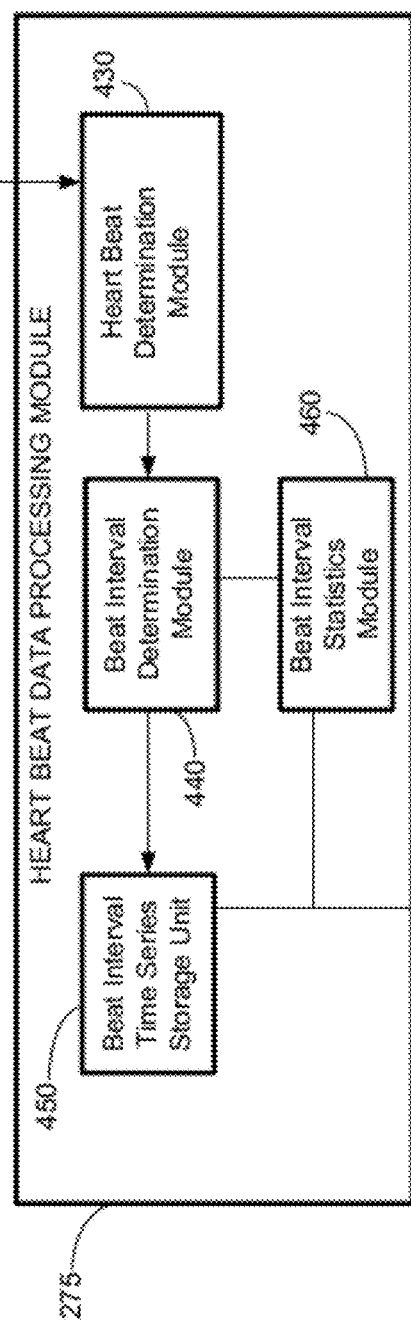
FIG. 3B is a stylized block diagram of a heart beat data processing module of a medical device, in accordance with one illustrative embodiment of the present invention.

Turning now to FIG. 3B, a more detailed stylized depiction of the heart beat data processing module 275 of FIG. 2, in accordance with one illustrative embodiment of the present invention is depicted. The heart beat data processing module 275 may comprise a heart beat determination module 430, a beat interval determination module 440, a beat interval time series storage unit 450, and a beat interval statistics module 460. The heart beat data processing module 275 may determine heart beats as they appear in the time series of signals via the heart beat determination module 430. For example, heart beat determination module 430 may characterize certain data points in the time series of signals as corresponding to the start, the peak, or the end of an R-wave of a patient's cardiac cycle.

Once heart beats are determined from the time series of signals, the beat interval determination module 440 may determine the interval between consecutive beats ("beat interval") and forward this information to beat interval time series storage 450. From the determined beat interval and/or the time series thereof, the beat interval statistics module 460 can determine various statistical (non-chaos) values of the beat interval time series, e.g., mean, median, or standard deviation, among others, for various timescales (e.g., 5 minutes, 1 hour, 24 hours). The beat interval time series, the statistical values thereof, or both may be used for further processing.

Figure 4:
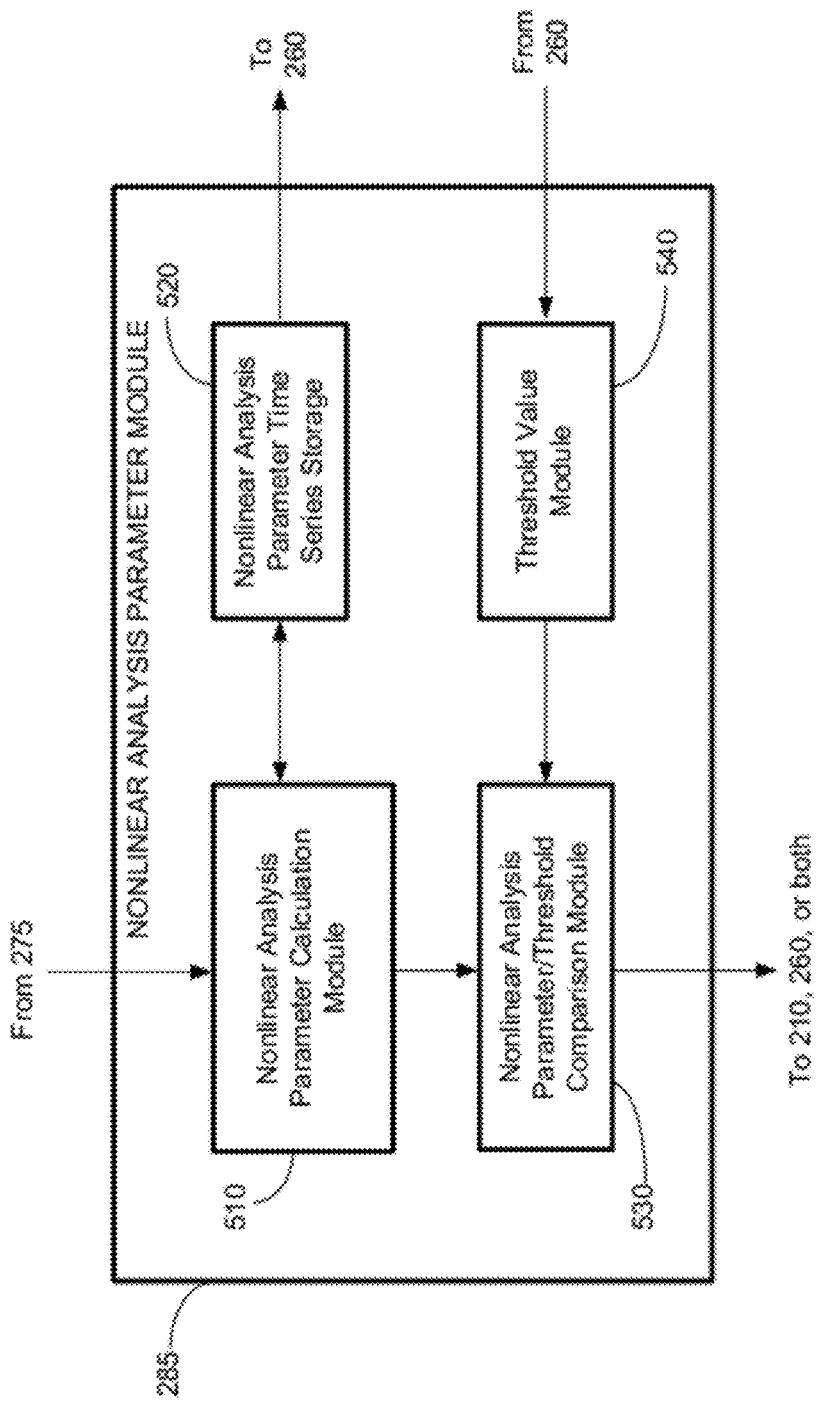
FIG. 4 is a block diagram of a nonlinear analysis module of a medical device, in accordance with one illustrative embodiment of the present invention.

Turning now to FIG. 4, a more detailed stylized depiction of the nonlinear analysis module 285 of FIG. 2, in accordance with one illustrative embodiment of the present invention is depicted. The nonlinear analysis module 285 may receive various data from the heart beat data processing module 275. Based upon data from the heart beat data processing module 275, the nonlinear analysis module 285 is capable of determining at least one nonlinear analysis parameter, such as those described above, and performing further calculations in light of the nonlinear analysis parameter, which may lead it to provide information to the controller 210. In one embodiment, the nonlinear analysis module 285 is capable of determining one or more nonlinear analysis parameters that indicate an actual or impending epileptic seizure, or a period of elevated risk of such a seizure. Based upon this determination, the nonlinear analysis module 285 may initiate one or more of several responsive actions, including generating an indication of at least one of an epileptic event or an impending epileptic event. This indication may be stored internally and/or externally, e.g., in the memory 217 (FIG. 2). This indication may also be transmitted to an external entity, e.g., to the monitoring unit 270 or an external device 610 (FIG. 5), and stored, e.g., into the local database unit 255 and/or the database unit 250 (FIG. 2). Nonlinear analysis module 285 may initiate other responsive actions such as providing an audible, visible, or tactile alert to the patient or a caregiver; logging a timestamp of the epileptic seizure; initiation of a seizure severity determination routine based upon data from the heart beat data processing module 275 and/or the nonlinear analysis module 285; communicating with one more ore of database unit 250 or remote device 292, or notifying emergency services via email or autophone communications. It may be appreciated that, based upon the output of the nonlinear analysis module, responsive action(s) may be performed by either the MD 200, monitoring unit 270, or other devices such as remote device 292.

In another embodiment, a preventive therapy or an interventive therapy may be performed as a responsive action. The therapy may comprise, for example, an electrical stimulation of the vagus nerve 127.

Returning to FIG. 4, the beat interval time series, its statistical values, or both are analyzed by a nonlinear analysis parameter calculation module 510, which determines the value of the at least one nonlinear analysis parameter of interest. The nonlinear analysis parameter calculation module 510 may store results in nonlinear analysis parameter time series storage 520, which may be a portion of the memory 217 or a separate memory unit. The nonlinear analysis parameter calculation module 510 may also access information from nonlinear analysis parameter time series storage 520 assess the dynamic of nonlinear analysis parameters or calculate derivative parameters. The nonlinear analysis parameter time series storage 520 may communicate nonlinear analysis parameter time series information to an monitoring unit 270 via communications unit 260.

After calculation module 510 calculates the at least one nonlinear analysis parameter of interest, nonlinear analysis parameter/threshold comparison module 530 may compare the calculated value to a threshold value. The threshold value used by the module 530 may be stored in threshold value module 540 after being placed there by a physician via communications unit 260 or after being calculated dynamically by the medical device 200. The threshold value used by the module 530 may be a portion of the memory 217 or a separate memory unit. In one embodiment, the threshold value module 540 may calculate a threshold value to provide an adaptive threshold rather than a fixed threshold. For example, thresholds may be calculated from a baseline chaos value for a particular patient that is determined from data stored in nonlinear analysis parameter time series storage 520, or other algorithms for determining a threshold may be implemented. In another embodiment, a nonlinear analysis parameter threshold may be modified based upon circadian rhythms of the patient.

Depending on the results of the comparison, the nonlinear analysis module 285 may provide information to controller 210 (if therapy is desired and the medical device 200 contains a stimulation unit 220 and associated hardware; if an indication of an epilepsy event is to be stored in memory 217, or both), to the communications unit 260 (if reporting of an indication of an epilepsy event via monitoring unit 270 to a physician, a database, etc. is desired), and/or to both.

Figure 5:
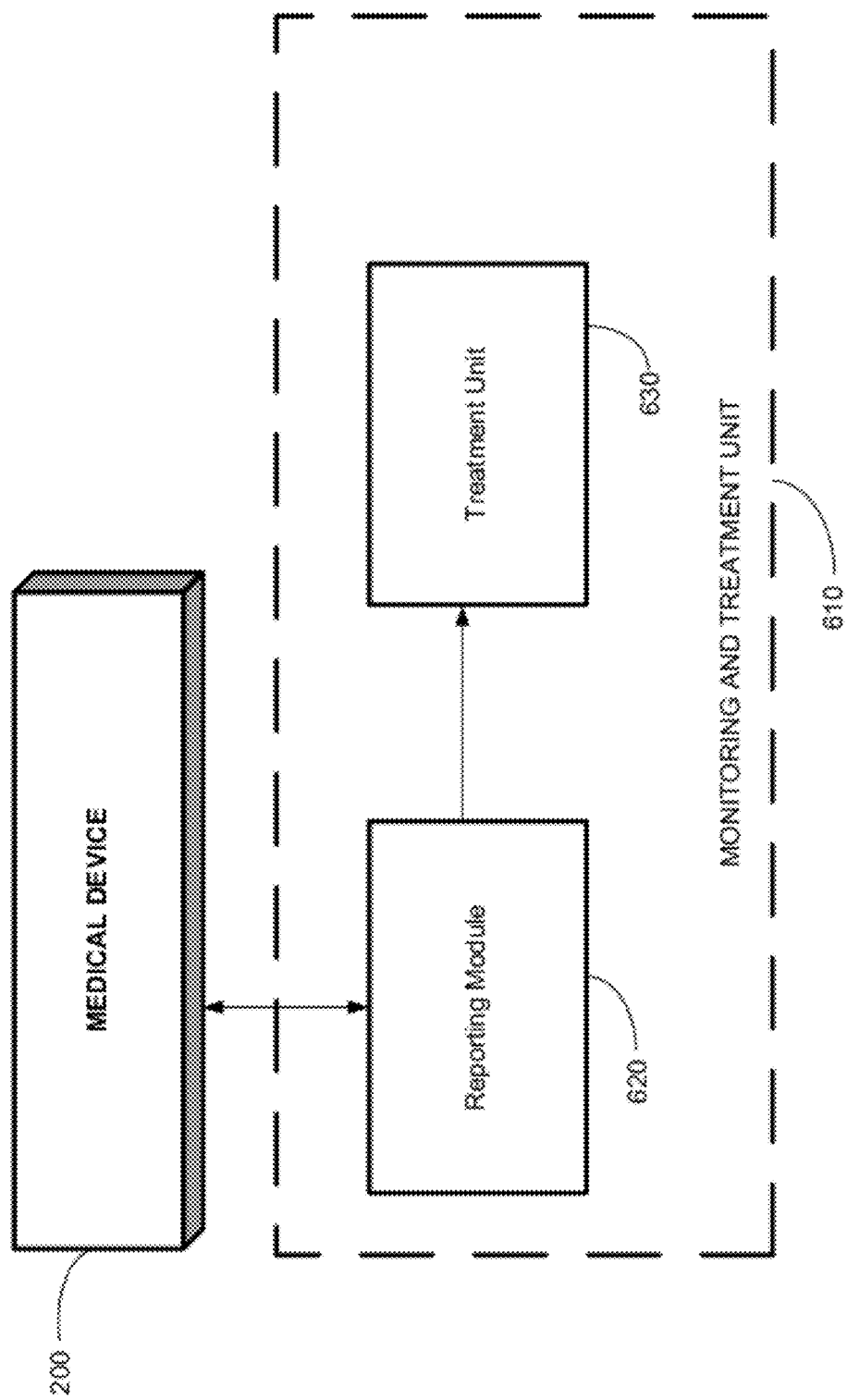
FIG. 5 is a block diagram of a medical device system external device, in accordance with one illustrative embodiment of the present invention.

Alternatively or in addition, according to one embodiment of the present invention as shown in FIG. 5, a monitoring and treatment unit 610, which may be an monitoring unit 270 or a unit other than medical device 200 implanted in or on the patient's body. The monitoring and treatment unit 610 may comprise a reporting module 620 to receive an indication of an occurring or impending epileptic event from the medical device 200 and a treatment unit 630 that can provide a therapy, such as an electrical signal to a neural structure of a patient, a drug delivery device, or a device that can cool a neural structure of a patient. In one embodiment, the medical device 200 may be external to the patient's body and the monitoring and treatment unit 610 may comprise a wholly or partially implanted system. More specifically, treatment unit 630 may be an implanted unit with programmed electrical parameters (e.g., amplitude, pulse width, frequency, on-time, off-time, etc.) that defines a therapeutic stimulation signal provided by a stimulation unit 220 (FIG. 2) to the electrodes 128 via the leads 201 (FIG. 2). Reporting module 620 may be implanted or external to the patient's body.

Figure 6:
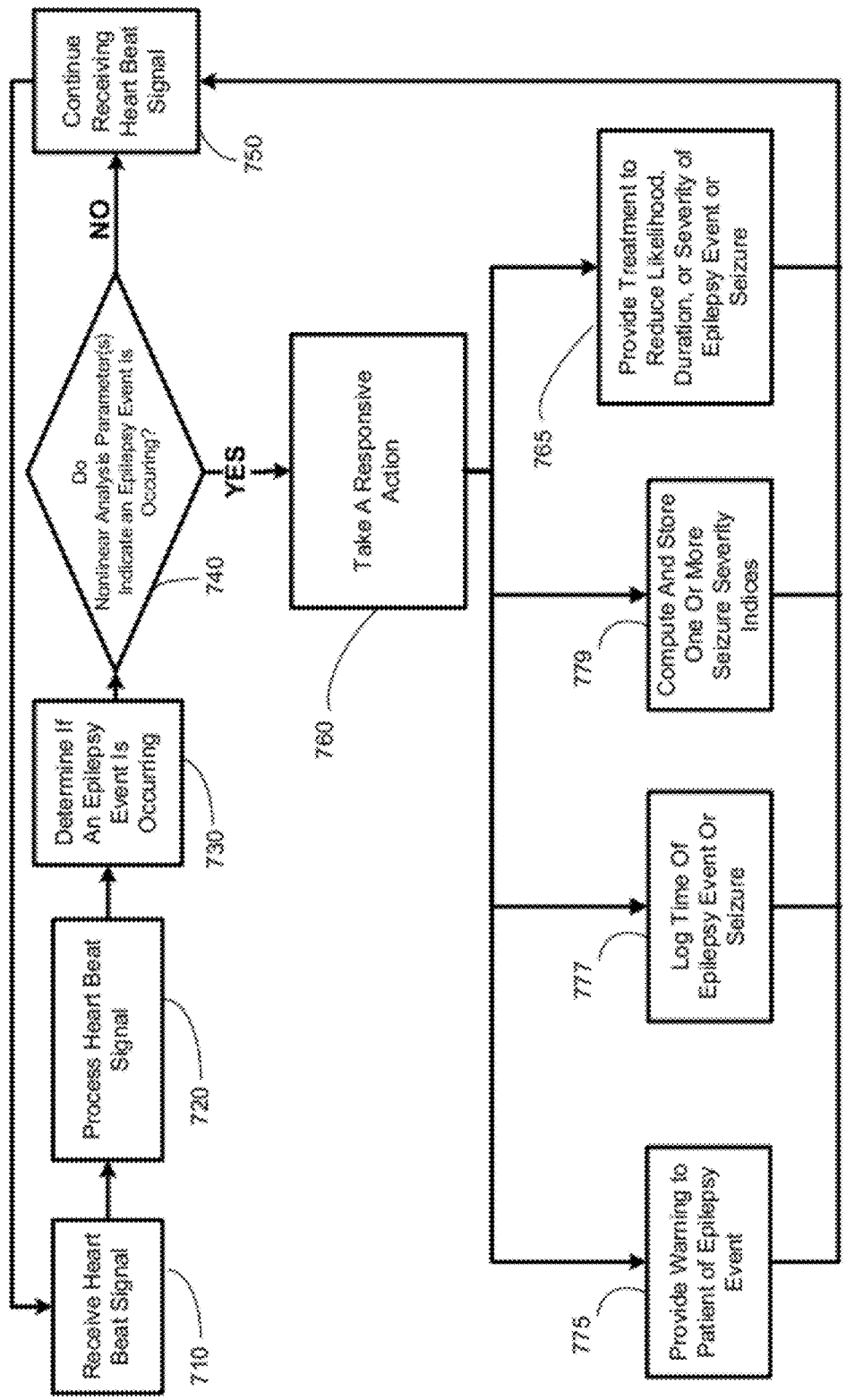
FIG. 6 illustrates a flowchart depiction of a method for detecting an epilepsy event, in accordance with an illustrative embodiment of the present invention.

Turning now to FIG. 6, a stylized flowchart depiction of detecting an epilepsy event, in accordance with one illustrative embodiment of the present invention, is provided. The medical device 200 receives a heart beat signal (block 710). Typically, the heart beat sensor interface 265 (FIGS. 2 and 3A) of the medical device 200 receives the heart beat signal. After performing buffering, amplification, filtering, and A/D conversion of the heart beat signal, the heart rate data processing module 275 processes the heart rate data for performing analysis of heart beat data (block 720). From the processing of the heart beat data, it is determined if an epilepsy event, such as an unstable brain state, an increased risk of a seizure, or a seizure is occurring (block 730). This determination may be performed by a nonlinear analysis module 285. A more detailed description of the step of determining if an epilepsy event is occurring is provided in FIG. 7 and the accompanying description below.

Based upon the determination (block 730), the medical device 200 decides whether the nonlinear analysis parameters indicate an epilepsy event is occurring (block 740). If no epilepsy event is occurring, the medical device 200 continues to receive the heart beat signal (block 750, returning flow to block 710).

However, if the medical device 200 determines that an epilepsy event is occurring in block 740, the medical device 200 or an external treatment unit 630 may take a responsive action selected from warning, logging the time of the seizure, computing and storing one or more seizure severity indices, and treating the epilepsy event (block 760). If treating is performed, it may reduce the duration, reduce the severity, or reduce the likelihood of a seizure. A "reduced duration" should be apparent to the person of ordinary skill in the art having benefit of the present disclosure. A "reduced severity" may be defined as a moderation of seizure-induced changes in heart rate (i.e., at least a partial reduction in tachycardia or bradycardia), a reduction in muscle activity, a reduction of one or more physiological impacts caused by the seizure, a subjective determination by the patient that the seizure is milder, or a shorter or milder post-ictal period, among others, wherein the reduced severity is relative to the patient's typical seizure in the absence of treatment. A more detailed description of step of providing a treatment is provided in FIG. 8 and accompanying description below. A reduced likelihood may be observed as a reduction in the frequency of seizures suffered by the patient in comparison to the frequency suffered prior to performance of the method.

Alternatively or in addition, the medical device 200 may provide a warning to the patient or his or her caregivers, physician, etc. (block 775); log a time of seizure (block 777); or compute and store one or more seizure severity indices (block 779). The warning may manifest as a warning tone or light implement by a nearby object adapted to receive indications of an impending epileptic event from the medical device 200; an automated email, text message, telephone call, or video message sent from the medical device 200, either directly or via an monitoring unit 270, to the patient's cellular telephone, PDA, computer, television, etc. Such a warning may allow the patient or his or her caregivers to take measures protective of patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc.

Figure 7:
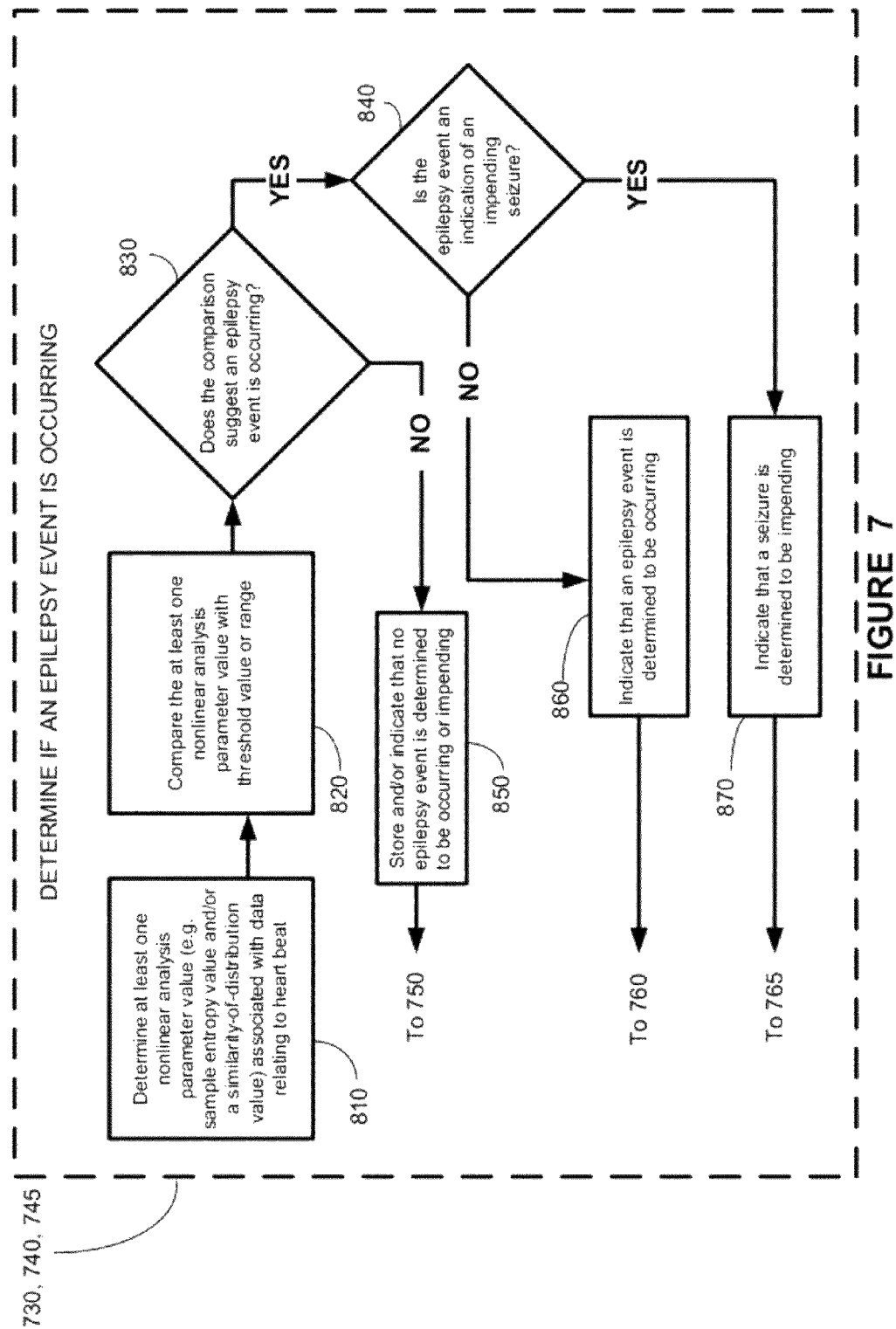
FIG. 7 illustrates a flowchart depiction of a determining step of the method depicted in FIG. 6, in accordance with an illustrative embodiment of the present invention.

Turning now to FIG. 7 a stylized flowchart depiction of determining whether nonlinear analysis parameters indicate an epilepsy event is occurring (blocks 730, 740, 745 of FIG. 6), according to one embodiment of the invention, is provided. At least one nonlinear analysis parameter value associated with heart beat data is determined (block 810). The nonlinear analysis parameter may be one of those described above; another found to be correlated with one of those described above; or another found after empirical observation to be useful. The at least one nonlinear analysis parameter value is then compared with a threshold value or range (block 820). As noted above, the threshold value may be a value that is predetermined by a user (e.g., a healthcare provider, the patient, etc.) based upon several factors. The threshold may be changed periodically or may be dynamically adjusted based upon various factors, such as the current physiological condition of the patient, the environment surrounding the patient, circadian rhythms; etc.

The comparison may suggest that an epilepsy event is occurring, and if yes, it may also suggest the epilepsy event is an indication of an impending seizure (blocks 830 and 840). The three possibilities (no epilepsy event, occurring epilepsy event, occurring seizure) yield corresponding indications (blocks 850, 860, and 870), which are then passed to downstream elements (e.g., block 740 of FIG. 6). That is, if the comparison of one or more nonlinear analysis parameter (correlated or otherwise) indicates that no epilepsy event is occurring, then an indication of such is stored and/or reported (block 850). If the comparison indicates that an epilepsy event is occurring, an indication of such is reported and/stored (block 860). If the comparison indicates that a seizure is impending, an indication of such is reported and/stored (block 880).

Figure 8:
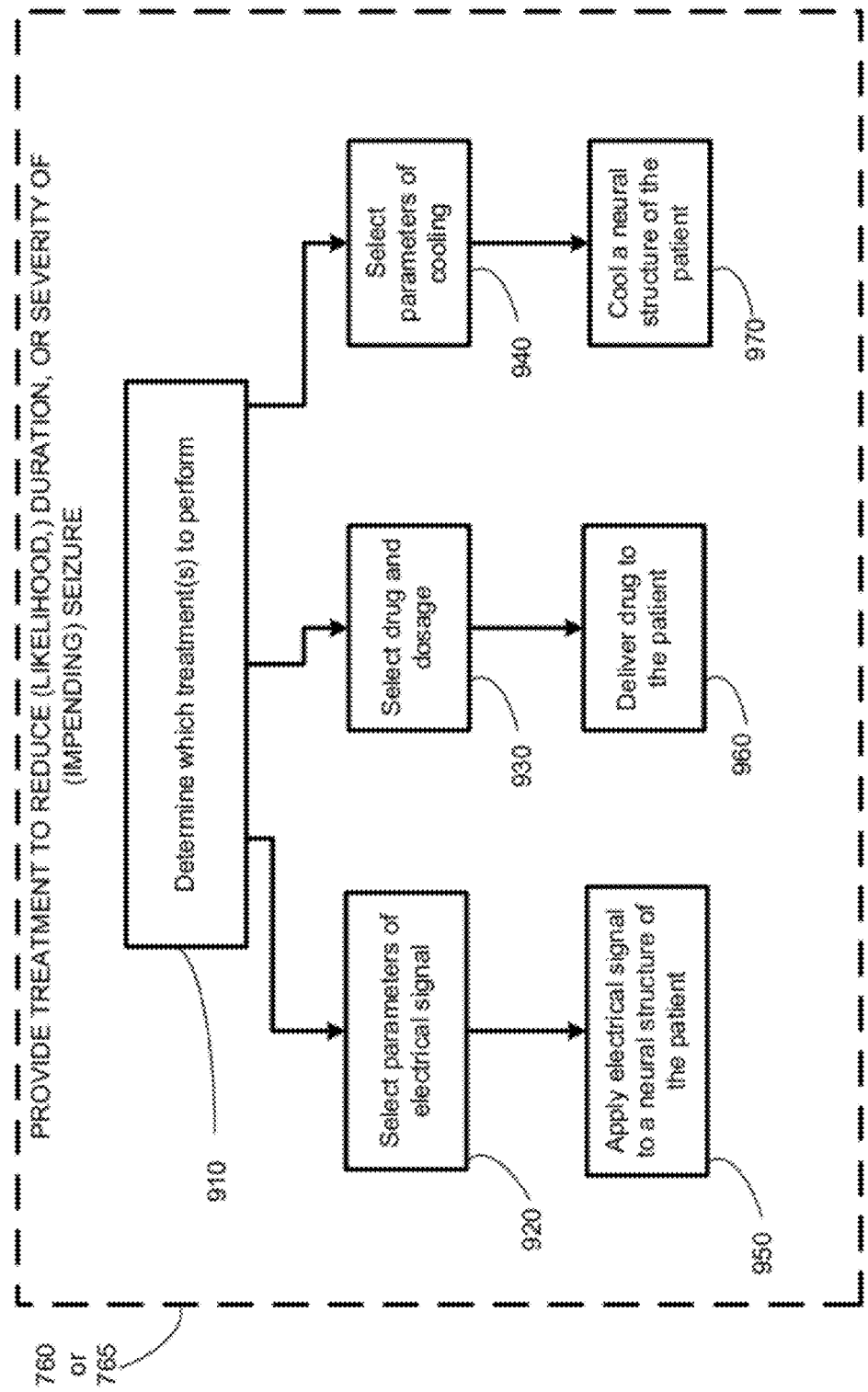
FIG. 8 illustrates a flowchart depiction of a providing step of the method depicted in FIG. 6, in accordance with an illustrative embodiment of the present invention.

Turning now to FIG. 8 a stylized flowchart depiction of providing a treatment based upon a determination that a seizure is occurring or impending (blocks 760 and 765 of FIG. 6), according to one embodiment of the invention, is provided. Upon determining that a seizure is occurring or impending, the medical device 200 determines which treatment(s) to perform (block 910). This determination is made based upon predetermined rules set up by a healthcare professional. For example, one result of a nonlinear analysis parameter threshold comparison described above may lead to a determination that only electrical signal treatment is required. However, during a more intense seizure, the threshold comparison may indicate that another type of treatment or a combination of treatments may be required. The treatments may be electrical signal therapy, drug therapy, and/or neural cooling therapy.

With regard to an electrical stimulation treatment, the parameters of electrical signal therapy (including an "on time" of zero milliseconds, i.e., the application of no electrical signals) are selected (block 920). Similarly, the drug and dosage of drug therapy (including a dosage of zero milligrams, i.e., the application of no drugs) are selected (block 930) and the parameters of cooling a neural structure (including the maintenance of the ambient temperature of the neural structure, i.e., no cooling) are selected (block 940). Thereafter, the electrical signal, drug, or cooling are applied, delivered, or performed (blocks 950, 960, and 970). The combination of treatment, if any, may be determined based upon the results of the comparison of the calculated nonlinear analysis parameter(s) to threshold values.

Particular embodiments may combine or eliminate or or more over the treatment therapies available. Thus, a given device may comprise only electrical signal therapy, only drug delivery therapy, or combinations of any of the foregoing therapies.

The above methods may be performed by a computer readable program storage device encoded with instructions that, when executed by a computer, perform the method described herein.

Figure 9:
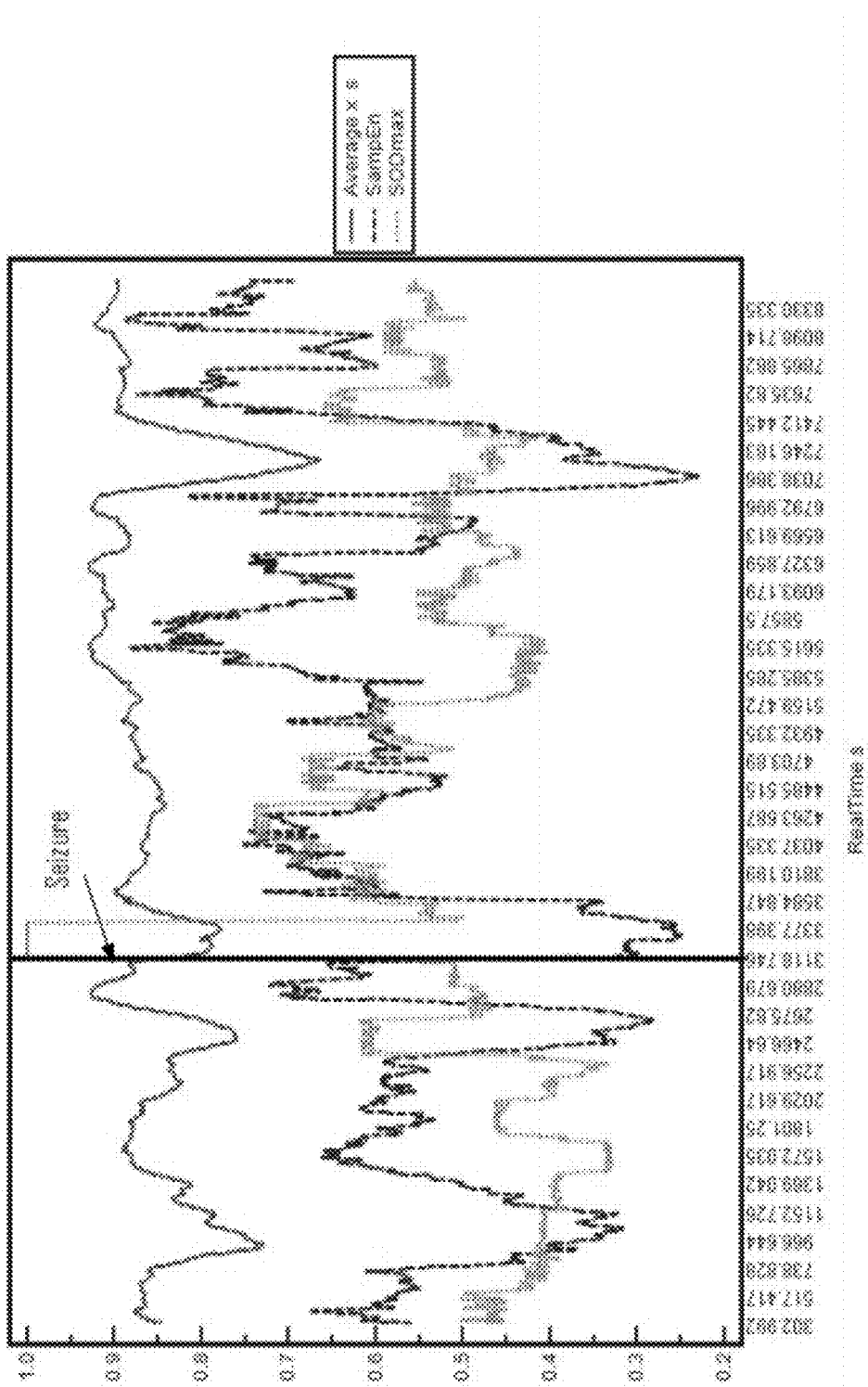
FIG. 9 illustrates a time series of observed values for sample entropy, similarity of distribution, and average inter-beat interval in a patient with diagnosed epilepsy.

FIG. 9 shows an example from a patient whose seizure was monitored in the clinic by an EEG machine. One channel of the EEG machine was used for collecting heart beat data (ECG). The SampEN (dashed line) and SOD (dotted line) were calculated retrospectively, but could have been calculated in real time with appropriate programming of appropriate devices.

As can be seen, the patient's SampEn value significantly decreased and SOD value simultaneously sharply rose at t=3109 second, just 28 sec after the electrophysiological onset of the seizure which was marked by a neurologist on the EEG.

Figure 10:
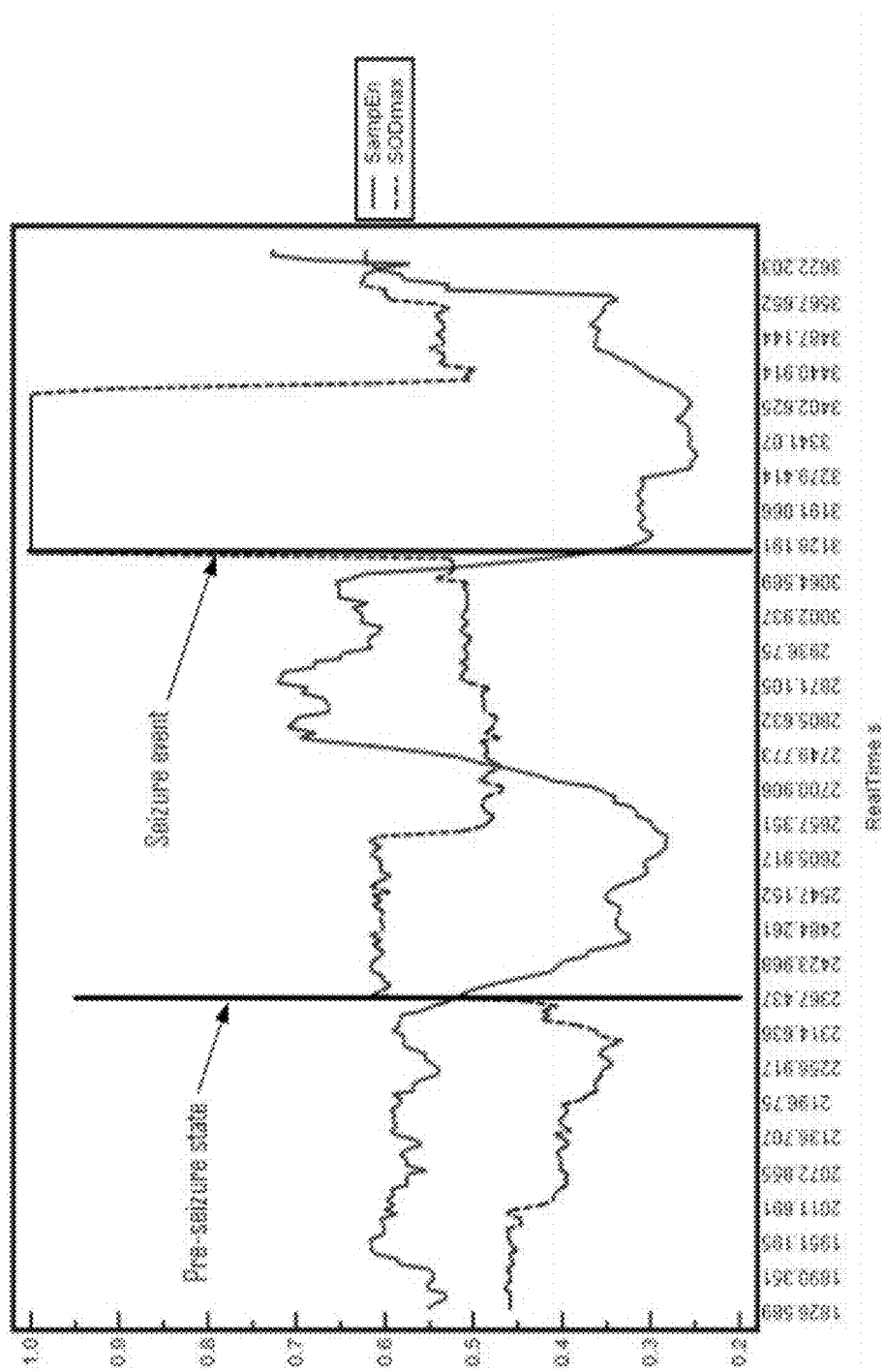
FIG. 10 illustrates a time series of observed values for sample entropy and similarity of distribution in the same patient as FIG. 9.

FIG. 10 shows a 30-second excerpt with pre-seizure and seizure events marked by the simultaneous decrease of SampEn and increase of SOD.

Figure 11:
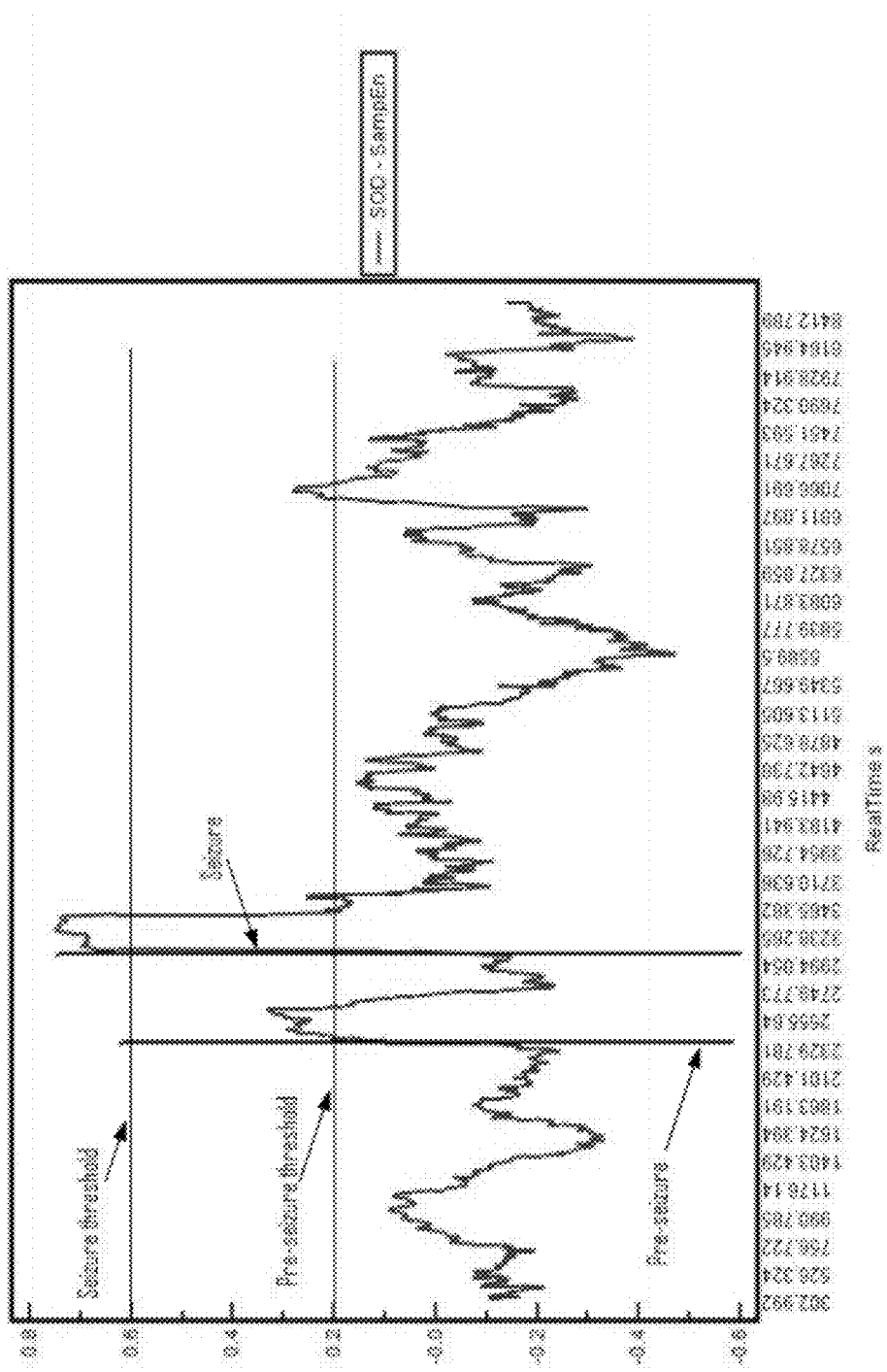
FIG. 11 illustrates a time series of observed values for similarity of distribution minus sample entropy of two and half hours of monitoring with detected and marked pre-seizure and seizure events based on threshold values in the same patient as FIG. 9.

FIG. 11 shows the same record as FIG. 9, but pre-seizure and seizure events are marked by the difference of SOD and SampEn values (SOD−SampEn). The detection is based on threshold values as 0.2 for pre-seizure event and 0.6 for seizure event. The pre-seizure event was detected 11 minutes before the seizure.

FIGS. 12-13 show the same record as FIG. 9, and show that statistical and spectral parameters derived from heart rate data provide poor specificity and poor sensitivity at detecting epilepsy events or seizures.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:
1. A method comprising:
   receiving data relating to a beat sequence of a patient's heart;
   determining at least one regularity nonlinear analysis parameter associated with the beat sequence of the patient's heart and at least one predictability nonlinear analysis parameter associated with the beat sequence of the patient's heart;

performing a first comparison of the at least one regularity nonlinear analysis parameter to a first adjustable threshold;

performing a second comparison of the at least one predictability nonlinear analysis parameter to a second adjustable threshold;

detecting an epilepsy event based on the first comparison and the second comparison, the epilepsy event comprising at least one of an unstable brain state, a brain state indicative of an elevated probability of a seizure, a brain state indicative of an impending seizure, and a seizure; and providing an output indicative of the epilepsy event.

2. The method of claim 1, wherein the at least one regularity nonlinear analysis parameter is sample entropy (SampEN) and the at least one predictability nonlinear analysis parameter is similarity of distribution (SOD), and wherein at least one of the first adjustable threshold and the second adjustable threshold is occasionally adjusted based in part on at least one of the patient's physiological condition, a patient's environment, and circadian rhythms.

3. A method comprising:
receiving data relating to a beat sequence of a patient's heart;
determining at least one regularity nonlinear analysis parameter associated with the beat sequence of the patient's heart;
performing a comparison of the at least one regularity nonlinear analysis parameter to an adjustable threshold;
detecting an epilepsy event based on the comparison, the epilepsy event comprising at least one of an unstable brain state, a brain state indicative of an elevated probability of a seizure, a brain state indicative of an impending seizure, and a seizure; and
providing an output indicative of the epilepsy event.

4. The method of claim 3, wherein the at least one regularity nonlinear analysis parameter is sample entropy (SampEN).

5. A method comprising:
receiving data relating to a beat sequence of a patient's heart;
determining at least one predictability nonlinear analysis parameter associated with the beat sequence of the patient's heart;
performing a comparison of the at least one predictability nonlinear analysis parameter to an adjustable threshold;
detecting an epilepsy event based on the comparison, the epilepsy event comprising at least one of an unstable brain state, a brain state indicative of an elevated probability of a seizure, a brain state indicative of an impending seizure, and a seizure; and
providing an output indicative of the epilepsy event.

6. The method of claim 5, wherein the at least one predictability nonlinear analysis parameter is similarity of distribution (SOD).

7. A method comprising:
receiving data relating to a beat sequence of a patient's heart;
determining at least one nonlinear analysis parameter associated with the beat sequence of the patient's heart;
performing a comparison of the at least one nonlinear analysis parameter to an adjustable threshold;
detecting an epilepsy event based on the comparison, the epilepsy event comprising at least one of an unstable brain state, a brain state indicative of an elevated probability of a seizure, a brain state indicative of an impending seizure, and a seizure; and
providing an output indicative of the epilepsy event.

8. The method of claim 7, wherein receiving the data relating to the beat sequence of the patient's heart comprises:
receiving a series of R-R intervals,
sensing a time of beat sequence of the patient's heart, and
generating a time series data stream from the time of the beat sequence, wherein
generating the time series data stream comprises:
sensing a plurality of R peaks from the R-R intervals, and
using the R peaks for providing a time stamp to generate the time series data stream based upon the time stamp.

9. The method of claim 7, wherein the adjustable threshold is adjustable using an external device.

10. The method of claim 7, wherein determining the at least one nonlinear analysis parameter comprises determining at least one of a complexity nonlinear analysis parameter and a stability nonlinear analysis parameter.

11. The method of claim 10, wherein the complexity nonlinear analysis parameter is an approximate entropy (ApproxEN) value or a sample entropy (SampEN) value associated with the data relating to the beat sequence and the stability nonlinear analysis parameter is a Similarity of distribution value associated with the data relating to the beat sequence.

12. The method of claim 7, further comprising taking a responsive action selected from providing a warning, logging a time of the seizure, computing and storing one or more seizure severity indices, and treating the epilepsy event based upon the comparison of the at least one nonlinear analysis parameter to the adjustable threshold.

13. The method of claim 12, wherein treating the epilepsy event comprises at least one of:
applying an electrical signal to a neural structure of the patient;
delivering a drug to the patient; and
cooling a neural structure of the patient.

14. The method of claim 13, wherein applying the electrical signal to the neural structure comprises applying the electrical signal to at least one of a brain structure of the patient, a cranial nerve of the patient, a spinal cord of the patient, a sympathetic nerve structure of the patient, and a peripheral nerve of the patient.

15. A medical device comprising:
a sensing module adapted to receive data relating to a beat sequence of a patient's heart;
a nonlinear analysis parameter processing module adapted to determine at least one nonlinear analysis parameter associated with the beat sequence of the patient's heart, adapted to perform a comparison of the at least one nonlinear analysis parameter to an adjustable threshold, and adapted to detect an epilepsy event based on the comparison, the epilepsy event including at least one of an unstable brain state, a brain state indicative of an elevated probability of a seizure, a brain state indicative of an impending seizure, and a seizure; and
a communication unit adapted to provide an output indicative of the epilepsy event.

16. The medical device of claim 15, further comprising:
a stimulation unit adapted to apply an electrical signal to a neural structure to treat the seizure, and a lead interface adapted to provide the electrical signal to a lead that is adapted to be operatively coupled to an electrode, wherein the electrode is adapted to couple to at least one of a portion of a brain structure of the patient, a cranial nerve of the patient, a spinal cord of the patient, a sympathetic nerve structure of the patient, and a peripheral nerve of the patient.

17. The medical device of claim 15, further comprising:
a threshold value module to store and to calculate the adjustable threshold; and
a memory unit to store at least a portion of a result of the comparison of the at least one nonlinear analysis parameter and the adjustable threshold.

18. The medical device of claim 15, wherein the adjustable threshold is adjustable using a device external to the patient.

19. The medical device of claim 15, wherein the nonlinear analysis parameter processing module is adapted to generate at least one of a complexity nonlinear analysis parameter and a stability nonlinear analysis parameter from the data relating to the beat sequence.

20. The medical device of claim 15, wherein the nonlinear analysis parameter processing module is adapted to determine at least one of a sample entropy value and a Similarity of distribution value based upon the data relating to the beat sequence.

21. The medical device of claim 15, further comprising:
a heart beat sensor unit adapted to receive a heart beat signal from a sensor; and
a heart beat data processing module adapted to process heart beat data based on the heart beat signal to determine various properties of a time series of the patient's heart beat.

22. The medical device of claim 21:
wherein the heart beat sensor unit comprises:
a heart beat signal receiver adapted to receive, amplify, and filter the heart beat signal;
an analog to digital converter to convert the heart beat signal into a digital form to provide the heart beat data; and
a heart beat correlation unit to organize the heart beat data and provide a time series of heart beats; and
wherein the heart beat data processing module comprises:
a heart beat determination module adapted to determine heart beats as they appear in the time series of heart beats;
a beat interval determination module adapted to determine an interval between consecutive heart beats;
a beat interval time series storage to receive beat interval data from the beat interval determination module and store the beat interval data; and
a beat interval statistics module adapted to determine one or more statistical values based on the beat interval data.

23. A computer readable program storage device encoded with instructions that, when executed by a processor, cause the processor to:
receive data relating to a beat sequence of a patient's heart;
determine at least one nonlinear analysis parameter associated with the beat sequence of the patient's heart;
perform a comparison of the at least one nonlinear analysis parameter to an adjustable threshold;
detect an epilepsy event based on the comparison, the epilepsy event comprising at least one of an unstable brain state, a brain state indicative of an elevated probability of a seizure, a brain state indicative of an impending seizure, and a seizure; and
provide an output indicative of the epilepsy event.

24. The computer readable program storage device of claim 23, wherein the instructions are further executable to cause the processor to take a responsive action selected from providing a warning, logging a time of the seizure, computing and storing one or more seizure severity indices, and treating the epilepsy event based upon the comparison of the at least one nonlinear analysis parameter to the adjustable threshold.

25. The computer readable program storage device of claim 24, wherein the treating the epilepsy event includes at least one of:
applying an electrical signal to a neural structure of the patient;
delivering a drug to the patient; and
cooling the neural structure of the patient.

26. The computer readable program storage device of claim 25, wherein applying the electrical signal to the neural structure of the patient comprises at least one of applying a deep brain stimulation (DBS) signal to a brain structure and applying the electrical signal to a cranial nerve of the patient.

27. A medical system comprising:
a sensing module adapted to receive data related to a beat sequence of a patient's heart;
a nonlinear analysis parameter processing module adapted to determine at least one nonlinear analysis parameter associated with the beat sequence of the patient's heart, to perform a comparison of the at least one nonlinear analysis parameter to an adjustable threshold, and to detect an epilepsy event based on the comparison, the epilepsy event comprising at least one of an unstable brain state, a brain state indicative of an elevated probability of a seizure, a brain state indicative of an impending seizure, and a seizure; and
a storage unit to store an indication of the epilepsy event.

28. The medical system of claim 27, further comprising a communications module adapted to communicate the indication to at least one of the patient, a caregiver, and a healthcare provider.

29. The medical system of claim 27, further comprising;
a threshold value module to store and to calculate the adjustable threshold; and
a stimulation unit adapted to apply an electrical signal to a neural structure to treat an impending epilepsy event based upon the comparison of the at least one nonlinear analysis parameter to the adjustable threshold.

30. The medical system of claim 27, further comprising a stimulation unit adapted to apply an electrical signal to a neural structure to treat the epilepsy event based upon the comparison of the at least one nonlinear analysis parameter to the adjustable threshold.

31. The medical system of claim 27, wherein the sensing module is part of an implantable medical device that is adapted to be implanted into a body of the patient, and wherein the medical system further comprises a communications interface module that is external to the body of the patient, wherein the communications interface module is adapted to communicate with a communications module in the implantable medical device.

32. The medical system of claim 31, wherein the nonlinear analysis parameter processing module is external to the body of the patient.

* * * * *